United States Patent [19]

Krüger et al.

[11] 4,341,551

[45] Jul. 27, 1982

[54] 1,2,3,-THIADIAZOLE-5-CARBOXYLIC ACID DERIVATIVES

[75] Inventors: Hans-Rudolf Krüger; Friedrich Arndt; Dietrich Baumert; Reinhart Rusch, all of Berlin, Fed. Rep. of Germany

[73] Assignee: Schering AG, Berlin and Bergkamen, Fed. Rep. of Germany

[21] Appl. No.: 127,496

[22] Filed: Mar. 5, 1980

[30] Foreign Application Priority Data

Mar. 12, 1979 [DE] Fed. Rep. of Germany ....... 2909991

[51] Int. Cl.³ .................. A01N 43/82; C07D 285/06; C07D 417/06
[52] U.S. Cl. ........................................... 71/90; 71/73; 71/77; 71/78; 424/248.51; 424/269; 424/267; 424/270; 544/134; 546/209; 548/127

[58] Field of Search ........................ 546/209; 548/127; 71/73, 77, 78, 90; 424/269, 270, 267

[56] References Cited

U.S. PATENT DOCUMENTS 4,177,054 12/1979 Arndt et al. ............................ 71/90

OTHER PUBLICATIONS

Sidgwick, The Organic Chemistry of Nitrogen, (Taylor et al. edition, Oxford, 1937), pp. 151–156.

*Primary Examiner*—Alton D. Rollins
*Attorney, Agent, or Firm*—Michael J. Striker

[57] ABSTRACT

A process for producing compounds of 1,2,3-thiadiazole-5-carboxylic acid is described. These compounds are effective as herbicides, fungicides and plant growth controllers.

93 Claims, No Drawings

1,2,3,-THIADIAZOLE-5-CARBOXYLIC ACID DERIVATIVES

BACKGROUND OF THE INVENTION

The present invention relates to novel 1,2,3-thiadiazole-5-carboxylic acid derivatives, a process for making these compounds, and such preparations which, when incorporated with these compounds, act as herbicides, fungicides and growth controlling agents.

In the plant cultivation, the weed killing process performs three essential functions. It assures a high yield, guarantees the usefulness of the crop and improves the operation conditions. The modern process of week killing is instrumental in causing full mechanization of the part of the operation as well as introduction of new technology. These new improvements have greatly influenced the farm and nursery trade and the advancement of technology in this area has caused such a great demand for these herbicides that it can not be easily fulfilled.

SUMMARY OF THE INVENTION

It is an object of the present invention to provide compounds which have improved weed killing properties.

To achieve this object and in accordance with its purpose, as embodied and broadly described, the present invention provides a preparation which contains at least one compound having the following general formula:

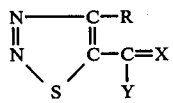

wherein R=hydrogen, $C_1$-$C_4$ alkyl, halogen-$C_1$-$C_4$ alkyl, $C_1$-$C_4$ alkyl mercapto $C_1$-$C_4$ alkyl, $C_1$-$C_4$ alkoxy $C_1$-$C_4$ alkyl,
and Y=hydrogen, the amino group:

wherein $R_1$=$R_2$=Hydrogen, when necessary a substituted $C_1$-$C_{18}$ alkyl residue, when necessary a $C_2$-$C_8$ alkenyl or alkynyl residue, when necessary a substituted aryl $C_1$-$C_3$ alkylresidue, when necessary a condensed aromatic or cycloaliphatic ring containing $C_3$-$C_8$ cycloaliphatic hydrocarbon residue, when necessary a substituted $C_3$-$C_8$ cycloalkyl-$C_1$-$C_3$-alkyl residue, when necessary one or more $C_1$-$C_6$ alkyl and/or halogen and/or $C_1$-$C_6$ alkoxy and/or nitro group and/or trifluoromethyl group substituted aromatic hydrocarbon residue or $R_1$ and $R_2$ together with the adjoining N-atom of 3 to 7 member representing a heterocyclical ring, which still can hold further O, S- or N- atoms, preferably the morpholino, piperidino or pyrrolidino groups,
or the group —Z—$R_3$,
wherein Z is oxygen or sulfur and $R_3$ represents when necessary a substituted $C_1$-$C_6$ alkyl residue, when necessary a substituted $C_2$-$C_6$ alkenyl or alkynyl residue, when necessary a substituted $C_3$-$C_8$ cycloalkyl residue, when necessary a substituted aryl $C_1$-$C_3$ alkyl residue and when necessary s substituted aryl residue
and X represents the imino group $$=N-R_2^1$$

or its salts with inorganic or organic acids,
wherein $R_2^1$=$R_2$ or represents sulfur when Y is an amino group.

DETAILED DESCRIPTION OF THE INVENTION

The compounds exhibit surprisingly excellent soil and leaf herbicide effect against seed weeds and perennial weeds. The constitutionally analogous compounds also exhibit similar properties. To some extent the effect is systematic. The compounds are especially effective against the species of Digitalis, Trifolium, Portulaca, Papaver, Daucus, Kochia, Gypsophila, Lactua, Solanum, Eschholtzia, Cheiranthus, Phacelia, Euphorbia, Linum, Convolvulus, Brassica, Datura, Cichorium, Ipomoea, Setaria, Agrostis, Phleum, Alopecurus, Phalaris, Dactylis, Festuca, Arrhenaterum, Lolium, Bromus, Avena, Allium, Medicago, Stellaria, Senecio, Matricaria, Lamium, Centaurea, Amaranthus, Galium, Chrysanthemum, Polygonum, Sorghum, Echinochloa, Digitaria, Cyperus, Poa and others.

The effective application dose for weed killing is from 0.5 to 5.0 kg of compound per hectare.

A selective weed killing for example is possible in cultivations of grains, cotton, soya beans and plantations. These compounds are most effective when they are sprayed over the existing weeds or before these weeds germinate. The seeds of cultivations mentioned above can sowed a few days after the spraying.

The compounds of the present invention can also change the natural development of the plants to obtain various useful landscape or horticultural properties. It is understood that a compound does not affect different plants in the same manner and its effect is dependent upon the method, time and concentration of the application. The compounds of the present invention can successfully be used upon seeds, germ (before or after the germination), roots, stalks, leaves, blossoms, fruits or other plant parts.

In general the growth pattern of natural plants can be visually recognized by noticing the change in size, shape, color or structure of the treated plant or its parts.

Examples of the changes caused by the compounds of the present invention are:
enlargement of leaves, arrest of vertical growth, inhibition of root development, stimulation of bud shoots and tiller, increased color intensity, and defoliation.

The compounds of the present invention are also effective against a variety of fungi, such as *plasmopara viticola, erysiphe cichoracearum, piricularia oryzae, helminthosporium gramineum* and *tilletia caries.*

It is highly important that the compounds of the present invention besides controlling the growth of plants also simultaneously destroy the plant pathogenic fungus. The compounds of the present invention can be used alone or in a preparation with other ingredients. Depending upon use the compounds could be mixed with other defoliants, herbicides and pesticides.

The compounds of the present invention can also be mixed with other biocides, which exhibit herbicidal properties. Examples of such biocides are: triazine group compounds, aminotriazole, anilide, diazine, uracile, aliphatic carboxylic acids and halogenated carboxylic acids, substituted benzoic acids and aryloxycarboxylic acids, hyderazide, amide, nitrile, their carboxylic acid esters, carbamide acid and thiocarbamide acid ester, urea, 2,3,6-trichlorobenzyloxy propanil, thiocyanogens and other ingredients.

The term "other ingredients" includes non-phytotoxic materials which act synergistically to increase the herbicidal effect. Some other materials which increase the effect are: wetting agents, emulsifiers, solvents and lubricants.

Depending upon the use, the compounds of the present invention or their preparations are made and applied in various forms such as powders, dust, pellets, solutions, emulsions and suspensions. Other additives such as liquid or solid carriers, diluents, wetting agents, binding agents, emulsions and dispersants can also be used.

Examples of suitable liquid carriers are: water, aliphatic and aromatic hydrocarbons such as benzene, toluene, xylene, cyclohexanone, Isophorone, dimethylsulfoxide, dimethyl formamide and mineral oil fractions.

Some examples of suitable solid carriers or substrates are: mineral earths such as tonsil, silica gel, talc, kaolin, attaclay, limestone, silicic acid and plant products such as meals (pulps).

Examples of surface active materials used are: calcium lignin sulfonate, polyoxyethylene-alkyl phenolether, naphthalin sulfonic acids and their salts, phenolsulfonic acids and their salts, formaldehyde condensate, fatty alcohol sulfates and substituted benzene sulfonic acids and their salts. The amount of effective compound in various preparations can vary widely. For example, the preparation may contain 10 to 18 percent by weight of the effective compounds, and 90 to 20 percent by weight liquid or solid carriers, and if desired the preparation may also contain 20 percent by weight of surface active agents.

The preparation can be applied in conventional manner. With water as the carrier, a quantity of about 100 to 1000 liters per hectare is effective. The preparation can be applied by the so-called low-volume and ultra low-volume process, and also in the form of so-called micro pellets.

The compounds of the present invention are more particularly effective when in the general formula: $R_1$=hydrogen, or when necessary it is substituted $C_1$-$C_4$ alkyl, such as methyl, ethyl, propyl, chloromethyl, bromomethyl, methylthiomethyl and methoxymethyl when X=sulfur or the imino group $R_1{}^1$-N and the rest $R_1$ and $R_2$ are hydrogen, $C_1$-$C_{18}$ alkyl, such as methyl, ethyl, propyl, Isopropyl, n-Butyl, tert.-Butyl, 2,2-Dimethyl-1-propyl, n-Heptyl, n-Nonyl, n-Undecyl, n-Octadecyl, 3-Methylbutyl, 4-Methyl-2-pentyl, Isobutyl, 3,3-Dimethylbutyl, 2- Butyl or 3,3-Dimethyl-2-butyl, substituted $C_{1-18}$ alkyl such as 2-chloroethyl, 3-chloropropyl, 3 bromopropyl, 2 bromoethyl, 1-Phenoxy-2-propyl, 3-Dimethylaminopropyl, 2-Dimethylaminoethyl, 3-Diethylaminopropyl, Tetrahydrofurfuryl, ethoxycarbonylmethyl, Cyanomethyl, 2,2-Dimethoxyethyl or 2-ethoxyethyl, $C_3$-$C_8$-Cycloalkyl $C_1$-$C_3$-alkyl such as Cyclohexylmethyl, 4-Cyanocyclohexylmetyl, 4-Hydroxymethylcyclohexylmethyl, 4-Carboxylcyclohexylmethyl, 1-Hydroxycyclohexylmethyl, Cycloheptylmethyl, Cyclooctymethyl or Cyclopropylmethyl $C_2$-$C_8$-Alkenyl- or -Alkynyl, such as 2-Propenyl, 2-Butenyl, 2-Methyl-2-propenyl, 2-Propynyl or 3-ethyl-1-pentyn-3-yl, Aryl-$C_1$-$C_3$-alkyl, benzyl, 4-chloro benzyl, 3-chlorobenzyl, 2-chlorobenzyl, 4-fluorobenzyl, 3-fluorobenzyl, 2-fluorobenzyl, 4-methylbenzyl, 3-methylbenzyl, 2-methylbenzyl, 3,4-methylenedioxybenzyl, 2,4-dichlorobenzyl, 3,4-dichlorobenzyl, 4-methoxybenzyl, 3-methoxybenzyl, 2-Methoxybenzyl, 2-Pyridylmethyl, 3-Pyridylmethyl, 4-Pyridylmethyl, α,α-Dimethylbenzyl, 1-Phenylethyl, 2-Phenylethyl, 1,2-Diphenylethyl, 2,2-Diphenylethyl, 4-Fluor-a-methylbenzyl, 3-phenylpropyl or 2-furfuryl, $C_3$-$C_8$-Cycloaliphatic hydrocarbon residue such as Cyclopropyl, Cyclopentyl, Cyclohexyl, 2-Methylcyclohexyl, 3-Methylcyclohexyl, 3-Methylcyclohexyl, 4-Methylcyclohexyl, 1,2,3,4-Tetrahydro-1-naphthyl, 1-ethynylcyclohexyl, Cycloheptyl or Cyclooctyl, aromatic hydrocarbon residue such as phenyl, 3-chlorophenyl, 2-chlorophenyl, 4-chlorophenyl, 2,4-dichlorophenyl, 4-fluorophenyl, 2-methylphenyl, 3-methylphenyl, 4-methylphenyl, 1-Naphthyl, 2-Methoxyphenyl, 3-Methoxyphenyl or 4-nitrophenyl.

$R_3$ represents such residues as $C_1$-$C_6$ alkyl residues, Methyl, Ethyl, Propyl, Isopropyl, n-Butyl, tert.-Butyl, 2,2-Dimethyl-1-propyl, n-Hexyl, Cyanoethyl, 2-Chloroethyl, 3-Chloropropyl, 2-Bromoethyl, 3-Dimethylaminopropyl, 2-Dimethylaminoethyl, 3-Diethylaminopropyl, 2,2-Dimethoxyethyl or 2-ethoxyethyl, as $C_2$-$C_6$ alkenyl or alkynyl residue, 2-propenyl, 2-Butenyl, 2-Methyl-2-propenyl or 2-Propynyl, as $C_3$-$C_8$-Cycloalkyl residue Cyclopropyl, Cyclobutyl, Cyclopentyl, Cyclohexyl, Cycloheptyl, Cyclooctyl, 4-Methylcyclohexyl, as Aryl-$C_1$-$C_3$ alkyl residue benzyl, 4-chlorobenzyl, 3-chlorobenzyl, 2-chlorobenzyl, 4-fluorobenzyl, 4-methylbenzyl, 3-methylbenzyl, 2-methylbenzyl, 3,4-methylenedioxybenzyl, 2,4-dichlorobenzyl, 3,4-dichlorobenzyl, 4-Methoxybenzyl, 3-Methoxybenzyl or 2-Methoxybenzyl, as aromatic hydrocarbon residue phenyl, 4-chlorophenyl, 4-methylphenyl, 3,4-dichlorophenyl, 3-trifluoromethyl, 4-bromophenyl, 4-fluorophenyl, 4-nitrophenyl, where Z=oxygen and/or sulfur and Y=halogen and preferably chlorine or bromine.

In the weed killing process compounds which are of exceptional importance are those in which the symbols in the general formula are represented as follows:

R=hydrogen or methyl, Y=chlorine, methylamino, ethylamino, tert. butylamino, methylpropylamino, N,N-diethylamino, allylamino, N,N-Diallylamino, Cyclohexylamino, Phenylamino, Methylphenylamino, Halogenphenylamino, dichlorophenylamino, Chloromethylphenylamino, Nitrophenylamino, N-Phenyl-N-methylamino, N,N-Diphenylamino, Cyclohexylmethylamino, Methylmercapto, Ethylmercapto, Phenylmercapto, Methylphenylmercapto, Benzylmercapto or Chlorobenzylmercapto and X=Phenylimino, Methylphenylimino, Dimethylphenylimino, Halogenphenylimino, Dihalogenphenylimino, Chloromethylphenylimino, Benzylimino, Halogenbenzylimino, Cyclohexylmethylimino or when Y=amino group the X=sulfur.

The compounds of the present invention are obtained in the following manner:

(A) When X=imino group and Y=halogen and R is represented by the radicals noted above, the compounds of the following general formula:

$$\begin{array}{c} N \!\!\!-\!\!\!-\!\! C\!-\!R \\ \| \quad \| \\ N \quad C\!-\!C\!-\!NH\!-\!R'_2 \\ \diagdown\!S\!\diagup \quad \| \\ \quad\quad O \end{array}$$

are reacted with halogenating agents, preferably thionylchloride, phosgene, phosphorus oxychloride, phosphorus pentachloride or triphenylphosphine mixed with tetrahalogenmethane.

(B) When Y=amino group and X=Sulfur and R is represented by the radicals noted above, the compounds of the following general formula:

$$\begin{array}{c} N \!\!\!-\!\!\!-\!\! C\!-\!R \\ \| \quad \| \\ N \quad C\!-\!C\!-\!NH\!-\!R'_2 \\ \diagdown\!S\!\diagup \quad \| \\ \quad\quad O \end{array}$$

are reacted with phosphorus pentoxide or the compounds of the following general formula:

$$\begin{array}{c} N \!\!\!-\!\!\!-\!\! C\!-\!R \\ \| \quad \| \\ N \quad C\!-\!C\!=\!N\!-\!R'_2 \\ \diagdown\!S\!\diagup \quad | \\ \quad\quad Cl \end{array}$$

are reacted with hydrogen sulfide, and if necessary in the presence of acid binding agents.

(C) When X=imino group and Y represents the —Z—R$_3$ group, the compounds of the following general formula:

$$\begin{array}{c} N \!\!\!-\!\!\!-\!\! C\!-\!R \\ \| \quad \| \\ N \quad C\!-\!C\!=\!N\!-\!R'_2 \\ \diagdown\!S\!\diagup \quad | \\ \quad\quad Cl \end{array}$$

are reacted with the compounds of the general formula:

H—Z—R$_3$ in the presence of acid binding agent. When Z represents sulfur only then the compounds of the following general formula:

$$\begin{array}{c} N \!\!\!-\!\!\!-\!\! C\!-\!R \\ \| \quad \| \\ N \quad C\!-\!C\!-\!NH\!-\!R'_2 \\ \diagdown\!S\!\diagup \quad \| \\ \quad\quad S \end{array}$$

are reacted with the compounds of the following general formula:

Halogen—R$_3$ in the presence of acid binding agents.

(D) When X=imino group and Y=amino group and R is represented by the above mentioned radicals, the compounds of the following general formula:

$$\begin{array}{c} N \!\!\!-\!\!\!-\!\! C\!-\!R \\ \| \quad \| \\ N \quad C\!-\!C\!=\!N\!-\!R'_2 \\ \diagdown\!S\!\diagup \quad | \\ \quad\quad Cl \end{array}$$

are reacted with the compounds of the general formula:

$$H\!-\!N\!\!\begin{array}{c}\diagup R_1 \\ \diagdown R_2\end{array}$$

and if necessary in the presence of acid binding agent. R, R$_1$, R$_2$, R'$_2$, R$_3$, X and Z have the above mentioned values and the halogen atom is preferably chlorine.

The reactions are carried out at temperatures between 0° and 120° C., and in general at a temperature between the room temperature and the reflux temperature of the corresponding reaction mixture.

For the synthesis of the compounds of the present invention the reactants are mixed in equimolar quantities. Suitable reaction media are solvents which are inert to the reactants. They are: halogenated hydrocarbons such as methylene chloride, chloroform, carbon tetrachloride, aliphatic and aromatic hydrocarbons such as petroleum ether, cyclohexane, benzene, toluene and xylene, alcohols such as methanol and ethanol, ketones such as acetone, methylisobutylketone and isophorone, ethers such as diethyl ether, tetrahydrofuran and dioxan, and carboxylic acid nitrile such as acetonitrile.

Suitable acid acceptors are organic bases such as, triethylamine or N,N-dimethylaniline and pyridine bases or inorganic bases such as oxides, hydroxides and carbonates of alkaline earth and alkaline metals. Liquid bases such as pyridine can also be used as solvents at the same time.

When producing the corresponding amidines, the compounds themselves act as acid capturers because of their high basicity. By using this process the amidines are obtained as hydrohalides from which the amidines are released in the usual known manner.

The compounds of the present invention made by the above mentioned process are isolated from the reaction mixture by the usual methods such as distilling off the solutions at normal or at reduced pressure, precipitating with water or by fractional distillation.

The compounds of the present invention are as a rule colorless and odorless crystalline substances or colorless and odorless liquids which are not easily soluble in water and are partially soluble in aliphatic hydrocarbons such as petroleum ether and cyclohexane. These liquids are readily soluble in halogenated hydrocarbons such as chloroform and carbon tetrachloride, aromatic hydrocarbons such as benzene, toluene and xylene, ethers such as diethylethers, tetrahydrofuran and dioxan carboxylic acid nitriles such as acetonitrile, ketones such as acetone, alcohols such as methanol and ethanol, carboxylic acid amides such as dimethylformamide, sulfoxides such as dimethylsulfoxide. Suitable solvents for crystallization are cyclohexane, acetonitrile, alcohol and diisopropyl ether.

The starting material 1,2,3-thiadiazole-5 carboxylic acid amide of the general formula:

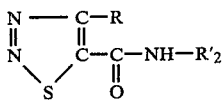

are generally known and can also be prepared by the known methods. The following examples fully illustrate manufacture of the compounds of the present invention.

EXAMPLE 1

4-Methyl-1,2,3-thiadiazole-5-(N-cyclohexylmethyl-carboximide chloride)

47.8 g (0.2 Mol) 4-Methyl-1,2,3-thiadiazole-5-carboxylic acid-(cyclohexylmethyl)-amide dissolved in 100 ml toluene are mixed with 41.6 g (0.2 mol) phosphorus pentachloride at room temperature and subsequently heated with reflux for 1 hour. The solution thereupon becomes concentrated and the residual oil is digested with cyclohexane. The compound is then crystallized out of cyclohexane.

Yield: 40.0 g=77.5% of theoretical colorless crystals
Fp: 51°–52° C.

Following analogies of the compounds of the present invention can be made:

| Name of the Compound | Physical Constants |
|---|---|
| 4-methyl-1,2,3, thiadiazole-5-[N-(3,4-dichlorophenyl)-carboximide chloride] | Fp.: 88–90° C. |
| 4-methyl-1,2,3-thiadiazole-5-[N-(4-chloro-2 methylphenyl)-carboximide chloride] | Fp.: 85–86° C. |
| 4-methyl-1,2,3-thiadiazole-5-[N-(3-chlorophenyl)-carboximide chloride] | Fp.: 57–59° C. |
| 4-methyl-1,2,3-thiadiazole-5-[N-(4-chlorophenyl)-carboximide chloride] | Fp.: 90–91° C. |
| 4-methyl-1,2,3-thiadiazole-5-[N-(2-methylphenyl)-carboximide chloride] | Fp.: 71–72° C. |
| 4-methyl-1,2,3-thiadiazole-5-[N-(3-methylphenyl)-carboximide chloride] | Fp.: 48–49° C. |
| 4-methyl-1,2,3-thiadiazole-5-[N-(4-methylphenyl)-carboximide chloride] | Fp.: 91–92° C. |
| 4-methyl-1,2,3-thiadiazole-5-[N-(4-fluorophenyl)-carboximide chloride] | Fp.: 79–80° C. |
| 4-methyl-1,2,3-thiadiazole-5-[N-(2-chlorophenyl)-carboximide chloride] | Fp.: 88–89° C. |
| 4-methyl-1,2,3-thiadiazole-5-[N-(4-chlorobenzyl)-carboximide chloride] | Fp.: 89–91° C. |
| 4-methyl-1,2,3-thiadiazole-5-[N-(4-fluorobenzyl) carboximide chloride] | Fp.: 48–49° C. |
| 4-methyl-1,2,3-thiadiazole-5-[N-phenyl carboximide chloride] | Fp.: 49–51° C. |
| 4-methyl-1,2,3-thiadiazole-5-[N-(2,6-dimethylphenyl)-carboximide chloride] | Fp.: 77–78° C. |

EXAMPLE 2

4-methyl-1,2,3-thiadiazole-5-thio carboxylic acid-(cyclohexyl methyl)-amide.

40 g (0.17 mol) 4-methyl-1,2,3-thiadiazole-5-carboxylic acid-(cyclohexyl methyl)-amide are dissolved in 350 ml toluene under boiling. Within 40 minutes 17.78 g (0.08 mol) are added to it and vigorously stirred under reflux heat. Upon cooling, it is decanted and the greasy residue in toluene is concentrated. The residue is warmed with 300 ml acetic ester to dissolve. Upon cooling the precipitated sulfur is filtered out and acetic acid filtrate concentrated. The remaining residue is crystallized with 250 ml. 250.

Yield=25.2 g=58.04% of theoretical
Fp.=69°–70° C-yellow crystals.

The following analogues of the compounds of the present invention can be made:

| Name of the Compound | Physical Constants |
|---|---|
| 4-methyl-1,2,3-thiadiazole-5-thio carboxylic acid benzylamide | $n_D^{20}$: 1,6648 |
| 4-methyl-1,2,3-thiadiazole-5-thio carboxylic acid-(3-methyl-cyclohexyl)-amide | Fp.: 95–97° C. |
| 4-methyl-1,2,3-thiadiazole-5-thio carboxylic acid-(2-methyl-cyclohexyl)-amide | Fp.: 123–124° C. |
| 4-methyl-1,2,3-thiadiazole-5-thio carboxylic acid-(fluorobenzyl)-amide | Fp.: 66–68° C. |
| 4-methyl-1,2,3-thiadiazole-5-thio carboxylic acid-(N-methyl-N-cyclohexylmethyl)-amide | Fp.: 82–83° C. |
| 4-methyl-1,2,3-thiadiazole-5-thio carboxylic acid-(1,2,3,4-tetrahydro-1-naphthyl)-amide | $n_D^{20}$: 1,6494 |
| 4-methyl-1,2,3-thiadiazole-5-thio carboxylic acid-(cycloheptyl-methyl)-amide | $n_D^{20}$: 1,6001 |
| 4-methyl-1,2,3-thiadiazole-5-thio carboxylic acid-(2-fluoro-benzyl)-amide | Fp.: 104–105° C. |
| 4-methyl-1,2,3-thiadiazole-5-thiocarboxylic acid-(cyclo-octylmethyl)-amide | $n_D^{20}$: 1,5955 |

EXAMPLE 3

4-methyl-1,2,3-thiadiazole-5-[N-cyclohexylmethyl thio carboximide acid methyl ester].

To a solution of 12.75 g (0.05 mol) 4-methyl-1,2,3-thiadiazole-5-thio carboxylic acid-(cyclohexylmethyl)-amide in 50 ml ethanol, drop by drop a solution of 2.0 g (0.05 mol) sodium hydroxide in 50 ml ethanol is added. The mixture is stirred for an hour and subsequently reacted with 7.1 g (0.05 mol) methyl iodide at 35° C. After a reaction time of 2 hours the solution is concentrated and the resulting residue is treated with water. After repetition it is agitated with ether. The ether extract is then dried over magnesium sulfate and concentrated, and the remaining oil is dried in vacuum at 40° C.

Yield: 13.2 g=98.2% of theoretical
$n_D^{20}$: 1.5651

The following analogues of the compounds of the present invention can be made:

| Name of the Compound | Physical Constants |
|---|---|
| 4-methyl-1,2,3-thiadiazole-5-[N-cyclohexylmethyl-thio-carboximide acid benzyl ester] | $n_D^{20}$: 1.5823 |
| 4-methyl-1,2,3-thiadiazole-5-[N-cyclohexylmethyl-thio-carboximide acid-(4-chlorobenzyl) ester] | Fp.: 58–60° C. |
| 4-methyl-1,2,3-thiadiazole-5-[N-cyclohexylmethyl-thio-carboximide acid ethyl ester] | $n_D^{20}$: 1.5551 |

EXAMPLE 4

4-methyl-1,2,3-thiadiazole-5-(N-cyclohexylmethyl-thio-carboximide acid phenyl ester)

5.1 ml (0.05 mol) thiophenol is added drop by drop to a solution of 2.8 g (0.05 mol) potassium hydroxide in 50 ml ethanol. To this solution 12.4 g (0.05 mol) 4-methyl-1,2,3-thiadiazole-5-(N-cyclohexylmethyl carboximide) chloride are added at 40° C. The mixture is stirred at 40° C. for 2 hours. It is then concentrated at 40° C. in vacuum. The residue is treated with 150 ml water and is then extracted twice with 75 ml of ether. The organic phase is then washed with saturated sodium hydrogen carbonate solution, dried over magnesium sulfate, filtered and concentrated.

Yield: 12.1 g = 72.9% of theoretical
$n_D^{20}$: 1.5960

The following analogues of the compounds of the present invention can be made:

| Name of the Compound | Physical Constants |
|---|---|
| 4-methyl-1,2,3-thiadiazole-5-[N-cyclohexylmethyl-thiocarboximide acid-(4-methylphenyl)-ester] | $n_D^{20}$: 1.5994 |
| 4-methyl-1,2,3-thiadiazole-5-[N-cyclohexylmethyl-thiocarboximide acid-(4-chlorophenyl)-ester] | $n_D^{20}$: 1.6073 |

EXAMPLE 5

$N^2$-(cyclohexylmethyl)-$N'$,$N'$-(diethyl)-4-methyl-1,2,3-thiadiazole-5-carboxamidine To a solution of 10.4 ml (0.1 mol) diethylamine in 50 ml tetrahydrofuran, 12.4 g (0.05 mol) 4-methyl-1,2,3-thiadiazole-5-(N-cyclohexylmethyl carboximide) chloride are introduced at 40° C. The mixture is stirred for 2 hours at 50° C. and the ensuing precipitate is filtered out. The filtrate is concentrated at 40° C. in vacuum and then treated with 150 ml water and then extracted 2 times with 75 ml ether. The extract is dried over magnesium sulfate and concentrated. The remaining oil is dried in vacuum at 40° C.

Yield: 14.4 g = 98.7% of theoretical
$n_D^{20}$: 1.5292

EXAMPLE 6

$N^2$-(cyclohexylmethyl)-$N'$-(phenyl)-4-methyl-1,2,3-thiadiazole-5-carboxamidine hydrochloride To a solution of 4.65 g (0.05 mol) aniline in tetrahydrofuran, 12.4 g (0.05 mol) of 4-methyl-1,2,3-thiadiazole-5-(N-cyclohexylmethyl carboximide chloride) are slowly introduced at 30° C. The mixture is left over night and then concentrated in vacuum at 40° C. It is then crystallized with acetonitrile.

Yield: 14.6 g = 83.5% of theoretical
Fp.: 209°–211° C. (decomposition) colorless crystals.
The following analogues of Examples 5 and 6 can be made:

| Name of the Compound | Physical Constants |
|---|---|
| $N^2$-Cyclohexylmethyl)-$N^1$-(phenyl)-$N^1$-(methyl)-4-methyl-1,2,3-thiadiazole-5-carboxamidine, hydrochloride | Fp.: 236° C. (decomposition) |
| $N^1$-(2-chlorophenyl)-$N^2$-(cyclohexylmethyl)-4-methyl-1,2,3-thiadiazole-5-carboxamidine, hydrochloride | Fp.: 231–32° C. (decomposition) |
| $N^1$-(3-chlorophenyl)-$N^2$-(cyclohexylmethyl)-4-methyl-1,2,3-thiadiazole-5-carboxamidine, hydrochloride | Fp.: 165–67° C. |
| $N^1$-(4-chlorophenyl)-$N^2$-(cyclohexylmethyl)-4-methyl-1,2,3-thiadiazole-5-carboxamidine, hydrochloride | Fp.: 212–15° C. (decomposition) |
| $N^2$-(cyclohexylmethyl)-$N^1$-(3,4-dichlorophenyl)-4-methyl-1,2,3-thiadiazole-5-carboxamidine hydrochloride | Fp.: 201–04° C. (decomposition) |
| $N^2$-(cyclohexylmethyl)-$N^1$-(2-methylphenyl)-4-methyl-1,2,3-thiadiazole-5-carboxamidine hydrochloride | Fp.: 232–33° C. (decomposition) |
| $N^2$-(cyclohexylmethyl)-$N^1$-(3-methylphenyl)-1,2,3-thiadiazole-5-carboxamidine hydrochloride | Fp.: 160–61° C. |
| $N^2$-(cyclohexylmethyl)-$N^1$-(4-methylphenyl)-4-methyl-1,2,3-thiadiazole-5-carboxamidine hydrochloride | Fp.: 221° C. (decomposition) |
| $N^2$-(cyclohexylmethyl)-$N^1$-(2,6-dichlorophenyl)-4-methyl-1,2,3-thiadiazole-5-carboxamidine hydrochloride | Fp.: 221–24° C. |
| $N^2$-(cyclohexylmethyl)-$N^1$-(3,5-dichlorophenyl)-4-methyl-1,2,3-thiadiazole-5-carboxamidine hydrochloride | Fp: 216° C. (decomposition) |
| $N^1$-(4-chloro-2-methylphenyl)-$N^2$-(cyclohexylmethyl)-4-methyl-1,2,3-thiadiazole-5-carboxamidine hydrochloride | Fp.: 202–05° C. (decomposition) |
| $N^2$-(cyclohexylmethyl)-$N^1$-(4-fluorophenyl)-4-methyl-1,2,3-thiadiazole-5-carboxamidine hydrochloride | Fp.: 209–10° C. (decomposition) |
| $N^2$-(cyclohexylmethyl)-$N^1$-(2-nitrophenyl)-4-methyl-1,2,3-thiazole-5-carboxamidine hydrochloride | Fp.: 208–09° C. (decomposition) |
| $N^1$-(2-chloro-6-methylphenyl)-$N^2$-(cyclohexylmethyl)-4-methyl-1,2,3-thiadiazole-5-carboxamidine hydrochloride | Fp.: 232–33° C. (decomposition) |
| $N^2$-(cyclohexylmethyl)-$N^1$-(phenyl)-4-methyl-1,2,3-thiadiazole-5-carboxamidine | Fp.: 105–06° C. |
| $N^2$-(4-chloro-2-methylphenyl)-$N^1$,$N^1$-(diethyl)-4-methyl-1,2,3-thiadiazole-5-carboxamidine | Fp.: 70–72° C. |
| $N^2$-(cyclohexylmethyl)-$N^1$,$N^1$-(diallyl)-4-methyl-1,2,3-thiadiazole-5-carboxamidine hydrochloride | Fp.: 172–73° C. (decomposition) |
| $N^2$-(3,4-dichlorophenyl)-$N^1$-(phenyl)-4-methyl-1,2,3-thiadiazole-5-carboxamidine | Fp.: 131–32° C. (decomposition) |
| $N^1$-(4-chloro-2-methylphenyl)-$N^2$-(phenyl)-4-methyl-1,2,3-thiadiazole-5-carboxamidine | Fp.: 152–53° C. |
| $N^1$-(2-chlorophenyl)-$N^2$-(4-chloro-2-methylphenyl)- | |

-continued

| Name of the Compound | Physical Constants |
|---|---|
| 4-methyl-1,2,3-thiadiazole-5-carboxamidine hydrochloride | Fp.: 178° C. (decomposition) |
| $N^2$-(cyclohexylmethyl)-$N^1$-(propyl)-4-methyl-1,2,3-thiadiazole-5-carboxamidine | Fp.: 41–42° C. |
| $N^1$-(butyl)-$N^2$-(cyclohexylmethyl)-4-methyl-1,2,3-thiadiazole-5-carboxamidine | Fp.: 63–65° C. |
| $N^1$-(tert.-butyl)-$N^2$-(cyclohexylmethyl)-4-methyl-1,2,3-thiadiazole-5-carboxamidine | Fp.: 70–72° -(1,1 |
| $N^1$-(cyclohexyl)-$N^1$-(methyl)-$N^2$-(cyclohexylmethyl)-4-methyl-1,2,3-thiadiazole-carboxamidine | Fp.: 107–08° C. |
| $N^1$-(ethyl)-$N^1$-(cyclohexyl)-$N^2$-(cyclohexylmethyl)-4-methyl-1,2,3-thiazole-5-carboxamidine | Fp.: 84–86° C. |
| $N^1$-(allyl)-$N^1$-(cyclohexyl)-$N^2$-(cyclohexylmethyl)-4-methyl-1,2,3-thiadiazole-5-carboxamidine | Fp.: 57–59° C. |
| $N^2$-(cyclohexylmethyl)-$N^1,N^1$-(diphenyl)-4-methyl-1,2,3-thiadiazole-5-carboxamidine | $n_D^{20}$: 1,5100 |
| $N^2$-(cyclohexylmethyl)-$N^1$-(1-methyl-propyl)-4-methyl-1,2,3-thiadiazole-5-carboxamidine | $n_D^{20}$: 1,5308 |
| $N^2$-(cyclohexylmethyl)-$N^1$-(2,3-dimethylphenyl)-4-methyl-1,2,3-thiadiazole-5-carboxamidine | Fp.: 87–88° C. |
| $N^2$-(cyclohexylmethyl)-$N^1$-(isopropyl)-4-methyl-1,2,3-thiadiazole-5-carboximidine | $n_D^{20}$: 1,5302 |
| $N^1$-ethyl-$N^1$-butyl-$N^2$-(cyclohexylmethyl)-4-methyl-1,2,3-thiadiazole-5-carboxamidine | $n_D^{20}$: 1,5232 |
| $N^1$-butyl-$N^1$-methyl-$N^2$-(cyclohexylmethyl)-4-methyl-1,2,3-thiadiazole-5-carboxamidine | $n_D^{20}$: 1,5271 |
| $N^2$-(cyclohexylmethyl)-$N^1,N^1$-(dibutyl)-4-methyl-1,2,3-thiadiazole-5-carboxamidine | $n_D^{20}$: 1,5145 |
| $N^1$-ethyl-$N^1$-isopropyl-$N^2$-(cyclohexylmethyl)-4-methyl-1,2,3-thiadiazole-5-carboxamidine | Fp.: 46–47° C. |
| $N^2$-(cyclohexylmethyl)-$N^1,N^1$-(dipropyl)-4-methyl-1,2,3-thiadiazole-5-carboxamidine | $n_D^{20}$: 1,5229 |
| $N^2$-(cyclohexylmethyl)-$N^1,N^1$-(diisobutyl)-4-methyl-1,2,3-thiadiazole-5-carboxamidine | $n_D^{20}$: 1,5166 |
| $N^2$-(cyclohexylmethyl)-N-(1,3-dimethylbutyl)-4-methyl-1,2,3-thiadiazole-5-carboxamidine | $n_D^{20}$: 1,5194 |
| $N^2$-(cyclohexylmethyl)-$N^1$-(1,1,3,3-tetramethylbutyl)-4-methyl-1,2,3-thiadiazole-5-carboxamidine | $n_D^{20}$: 1,5180 |
| $N^2$-(cyclohexylmethyl)-$N^1$-(3,5-dimethylphenyl)-4-methyl-1,2,3-thiadiazole-5-carboxamidine | Fp.: 90–91° C. |
| $N^2$-(cyclohexylmethyl)-$N^1$-(2,4-dimethylphenyl)-4-methyl-1,2,3-thiadiazole-5-carboxamidine | Fp.: 83–84° C. |
| $N^2$-(cyclohexylmethyl)-$N^1$-(2,5-dimethylphenyl)-4-methyl-1,2,3-thiadiazole-5-carboxamidine | $n_D^{20}$: 1,5769 |
| $N^2$-(cyclohexylmethyl)-$N^1$-(2,6-dimethylphenyl)-4-methyl-1,2,3-thiadiazole-5-carboxamidine | $n_D^{20}$: 1,5762 |
| $N^2$-(cyclohexylmethyl)-$N^1$-(3,4-dimethylphenyl)-4-methyl-1,2,3-thiadiazole-5-carboxamidine | Fp.: 100–101° C. |
| $N^1$-(benzyl)-$N^2$-(cyclohexylmethyl)-4-methyl-1,2,3-thiadiazole-5-carboxamidine | Fp.: 80–81° C. |
| $N^1,N^2$-bis(cyclohexylmethyl)-4-methyl-1,2,3-thiadiazole-5-carboxamidine | Fp.: 118–121° C. |
| $N^1$-(cyclohexyl)-$N^2$-(cyclohexylmethyl)-4-methyl-1,2,3-thiadiazole-5-carboxamidine | Fp.: 77–78° C. |
| $N^2$-(cyclohexylmethyl)-$N^1,N^{20}$-(tetramethylene)-4-methyl-1,2,3-thiadiazole-5-carboxamidine | $n_D^{20}$: 1,5518 |
| $N^2$-(cyclohexylmethyl)-$N^1,N^1$-(pentamethylene)-4-methyl-1,2,3-thiadiazole-5-carboxamidine | Fp.: 43–45° C. |
| $N^2$-(cyclohexylmethyl)-$N^1,N^1$-(diisopropyl)-4-methyl-1,2,3-thiadiazole-5-carboxamidine | Fp.: 93–94° C. |
| $N^2$-(cyclohexylmethyl)-$N^1,N^1$-(dihexyl)-4-methyl-1,2,3-thiadiazole-5-carboxamidine | $n_D^{20}$: 1,4668 |
| $N^2$-(cyclohexylmethyl)-$N^1$-(1,2,2-trimethylpropyl)-4-methyl-1,2,3-thiadiazole-5-carboxamidine | Fp.: 78–79° C. |
| $N^2$-(cyclohexylmethyl)-$N^1$-(3-methylbutyl)-4-methyl-1,2,3-thiadiazole-5-carboxamidine | Fp.: 72–74° C. |
| $N^1$-(ethyl)-$N^1$-(propyl)-$N^2$-(cyclohexylmethyl)-4-methyl-1,2,3-thiadiazole-5-carboxamidine | $n_D^{20}$: 1,5262 |
| $N^2$-(cyclohexylmethyl)-$N^1$-(1,1-dimethylpropyl)-4-methyl-1,2,3-thiadiazole-5-carboxamidine | Fp.: 64–71° C. |
| 4-methyl-5-[(cyclohexylmethylimino)-(imidazole-1-yl)-methyl]-1,2,3-thiadiazole | Fp.: 82–83° C. |
| 4-methyl-5-[(cyclohexylmethylimino)-(1,2,4-triazole-1-yl)-methyl]-1,2,3-thiadiazole | Fp.: 86–87° C. |
| $N^2$-(cyclohexylmethyl)-$N^1$-(1,2-dimethylpropyl)-4-methyl-1,2,3-thiadiazole-5-carboxamidine | $n_D^{20}$: 1,5251 |
| $N^1$-(allyl)-$N^2$-(cyclohexylmethyl)-4-methyl-1,2,3-thiadiazole-5-carboxamidine | Fp.: 44–46° C. |
| $N^1$-(ethyl)-$N^2$-(cyclohexylmethyl)-4-methyl-1,2,3-thiadiazole-5-carboxamidine | Fp.: 49–50° C. |
| $N^2$-(cyclohexylmethyl)-$N^1$-(methyl)-4-methyl-1,2,3-thiadiazole-5-carboxamidine | Fp.: 79–80° C. |
| $N^2$-(cyclohexylmethyl)-$N^1,N^1$-(dimethyl)-4-methyl-1,2,3-thiadiazole-5-carboxamidine | Fp.: 43–45° C. |
| $N^2$-(cyclohexylmethyl)-4-methyl-1,2,3-thiadiazole-5-carboxamidine hydrochloride | Fp.: 192–195° C. (decomposition) |
| $N^2$-(4-chloro-2-methylphenyl-$N^1,N^1$-(dimethyl)-4-methyl-1,2,3-thiadiazole-5-carboxamidine | Fp.: 98–99° C. |
| $N^2$-(4-chloro-2-methylphenyl)-$N^1$-(methyl)-4-methyl-1,2,3-thiadiazole-5-carboxamidine | $n_D^{20}$: 1,6088 |
| $N^1$-(methyl)-$N^2$-(methyl)-4-methyl-1,2,3-thiadiazole-5-carboxamidine | Fp.: 83–85° C. |
| $N^1,N^1$-(dimethyl)-$N^2$-(methyl)-1,2,3-thiadiazole-5-carboxamidine | Fp.: 43–45° C. |

EXAMPLE 7

In a hothouse, the compounds of the present invention were sprayed on the test plants Sinapis (Si), Solanum (So), *Beta Vulgaris* (Be), Gossypium (Go), Hordeum (Ho), *Zea mays* (Ze), Lolium (Lo) and Setaria (Se) in before (V) and after germination (N) process. The compounds were used as aqueous emulsions or suspensions in an effective dose of 5 kg of compound-/hectare and sprayed in a quantity of 600 liter water-/hectare. Three weeks after the treatment the results were noted and logged as follows:

O = no effect.

1-2 = growth controlling effect in form of intensive coloring of primary leaves, retardation, depression and reduction or enlargement of the leaves, deficient root development.

3-4 = withered, and no longer viable.

The results were tabulated as follows:

| Compound Name | Si V N | So V N | Be V N | Go V N | Ho V N | Ze V N | Lo V N | Se V N |
|---|---|---|---|---|---|---|---|---|
| 4-methyl-1,2,3-thiadiazole-5-(N-cyclohexyl-methyl-carboximide chloride) | 4 4 | 4 4 | 4 4 | 3 4 | 4 3 | 3 1 | 4 3 | 4 4 |
| 4-methyl-1,2,3-thiadiazole-5-[N-(3,4-dichlorophenyl)-carboximide chloride] | 0 1 | 0 2 | 0 1 | 0 0 | 0 0 | 0 0 | 0 0 | 1 1 |
| 4-methyl-1,2,3-thiadiazole-5-[N-(4-chloro-2-methylphenyl)-carboximide-chloride] | 1 1 | 1 1 | 1 1 | 1 1 | 0 0 | 0 0 | 0 0 | 1 1 |
| 4-methyl-1,2,3-thiadiazole-5-[N-(3,-chlorophenyl)-carboximide chloride] | 0 1 | 0 2 | 0 2 | 0 0 | 0 0 | 0 0 | 0 0 | 0 0 |
| 4-methyl-1,2,3-thiadiazole-5-[N-(4-chlorophenyl)-carboximide chloride] | 0 2 | 0 1 | 0 2 | 0 1 | 0 0 | 0 0 | 0 0 | 0 1 |
| 4-methyl-1,2,3-thiadiazole-5-[N-(2-methylphenyl)-carboximide chloride] | 0 1 | 0 1 | 0 0 | 0 0 | 0 0 | 0 0 | 0 0 | 0 0 |
| 4-methyl-1,2,3-thiadiazole-5-[N-(3-methylphenyl)-carboximide chloride] | 1 1 | 1 1 | 2 2 | 1 1 | 0 0 | 0 0 | 0 0 | 1 1 |
| 4-methyl-1,2,3-thiadiazole-5-[N-(4-methylphenyl)-carboximide chloride] | 1 1 | 1 1 | 1 1 | 0 1 | 0 1 | 0 1 | 0 1 | 0 1 |
| 4-methyl-1,2,3-thiadiazole-5-[N-(4-fluorophenyl)-carboximide chloride] | 0 1 | 0 0 | 0 1 | 0 0 | 0 0 | 0 0 | 0 0 | 0 1 |
| 4-methyl-1,2,3-thiadiazole-5-[N-(2-chlorophenyl)-carboximide chloride] | 0 2 | 0 1 | 0 2 | 0 1 | 0 0 | 0 0 | 0 0 | 0 1 |
| 4-methyl-1,2,3-thiadiazole-5-[N-(4-chlorobenzyl)-carboximide chloride] | 2 4 | 4 3 | 1 4 | 1 3 | 0 0 | 0 0 | 1 0 | 1 3 |
| 4-methyl-1,2,3-thiadiazole-5-[N-(4-fluorobenzyl)-carboximide chloride] | 3 4 | 4 4 | 4 4 | 3 4 | 4 1 | 3 0 | 4 0 | 4 4 |
| 4-methyl-1,2,3-thiadiazole-5-[N-phenyl-carboximide chloride] | 0 2 | 0 2 | 0 1 | 0 1 | 0 0 | 0 0 | 0 0 | 0 1 |
| 4-methyl-1,2,3-thiadiazole-5-[N-(2,6-dimethylphenyl)-carboximide chloride] | 1 0 | 1 0 | 0 0 | 0 1 | 0 0 | 0 0 | 0 0 | 0 2 |
| 4-methyl-1,2,3-thiadiazole-5-thiocarboxylic acid (cyclohexylmethyl)-amide | 4 4 | 4 4 | 4 4 | 3 4 | 3 1 | 2 1 | 4 3 | 4 4 |
| 4-methyl-1,2,3-thiadiazole-5-[N-cyclohexylmethyl-thiocarboximide acid methyl-ester[ | 4 4 | 4 4 | 4 4 | 3 4 | 3 3 | 3 2 | 4 4 | 3 4 |
| 4-methyl-1,2,3-thiadiazole-5-[N-cyclohexylmethyl-thiocarboximide acid benzyl-ester] | 2 4 | 4 4 | 1 4 | 2 4 | 3 1 | 2 2 | 4 1 | 2 3 |
| 4-methyl-1,2,3-thiadiazole-5-[N-cyclohexylmethyl-thiocarboximide acid-(4-chlorobenzyl)-ester] | 0 4 | 3 4 | 2 4 | 3 4 | 4 2 | 2 1 | 3 1 | 1 2 |
| 4-methyl-1,2,3-thiadiazole-5-[N-cyclohexylmethyl-thiocarboxymide acid ethyl-ester] | 2 4 | 4 4 | 3 4 | 3 4 | 3 2 | 2 2 | 3 2 | 1 4 |
| 4-methyl-1,2,3-thiadiazole-5-(N-cyclohexylmethyl-thiocarboximide acid phenyl-ester) | 4 4 | 4 4 | 4 4 | 3 4 | 4 3 | 3 3 | 4 2 | 4 4 |
| 4-methyl-1,2,3-thiadiazole-5-[N-cyclohexylmethyl-thiocarboximide acid-(4-methylphenyl)-ester] | 4 4 | 4 4 | 4 4 | 3 4 | 4 3 | 2 3 | 4 3 | 4 4 |
| $N^2$-(cyclohexylmethyl)-$N^1,N^1$-(diethyl)-4-methyl-1,2,3-thiadiazole-5-carboxamidine | 2 4 | 3 2 | 3 4 | 2 3 | 3 2 | 2 1 | 3 2 | 2 2 |
| $N^2$-(cyclohexylmethyl)-$N^1$-(phenyl)-4-methyl-1,2,3-thiadiazole-5-carboxamidine hydrochloride | 0 2 | 0 0 | 0 0 | 0 0 | 0 0 | 0 0 | 0 0 | 0 0 |
| $N^2$-(cyclohexylmethyl)-$N^1$-(phenyl)-$N^1$-(methyl)-4-methyl-1,2,3-thiadiazole-5-carboxamidine hydrochloride | 1 2 | 2 2 | 2 2 | 2 2 | 1 1 | 1 1 | 1 1 | 1 1 |
| $N^1$-(2-chlorophenyl)-$N^2$-(cyclohexylmethyl)-4-methyl-1,2,3-thiadiazole-5-carboxamidine hydrochloride | 0 1 | 0 2 | 0 2 | 0 1 | 0 0 | 0 0 | 0 0 | 0 1 |
| $N^1$-(3-chlorophenyl)-$N^2$-(cyclohexylmethyl)-4-methyl-1,2,3-thiadiazole-5-carboxamidine hydrochloride | 0 1 | 0 1 | 0 2 | 0 1 | 0 0 | 0 0 | 0 0 | 0 2 |
| $N^1$-(4-chlorophenyl)-$N^2$-(cyclohexylmethyl)-4-methyl-1,2,3-thiadiazole-5-carboxamidine hydrochloride | 1 2 | 1 1 | 0 1 | 0 1 | 0 1 | 0 0 | 0 0 | 0 1 |
| $N^2$-(cyclohexylmethyl)-$N^1$-(3,4-dichlorophenyl)-4-methyl-1,2,3-thiadiazole-5-carboxamidine hydrochloride | 0 1 | 0 2 | 0 1 | 0 1 | 0 0 | 0 0 | 0 0 | 0 1 |
| $N^2$-(cyclohexylmethyl)-$N^1$-(2-methylphenyl)-4-methyl-1,2,3-thiadiazole-5- | | | | | | | | |

-continued

| Compound Name | Si V N | So V N | Be V N | Go V N | Ho V N | Ze V N | Lo V N | Se V N |
|---|---|---|---|---|---|---|---|---|
| carboxamidine hydrochloride | 1 1 | 1 1 | 1 1 | 1 1 | 1 1 | 0 0 | 0 1 | 1 1 |
| N²-(cyclohexylmethyl)-N¹-(3-methyl-phenyl-1,2,3-thiadiazole-5-carboxamidine hydrochloride | 0 2 | 0 2 | 0 1 | 0 1 | 0 0 | 0 0 | 0 0 | 0 1 |
| N²-(cyclohexylmethyl)-N¹-(4-methyl-phenyl)-4-methyl-1,2,3-thiadiazole-5-carboxamidine hydrochloride | 0 1 | 0 2 | 0 1 | 0 1 | 0 1 | 0 0 | 0 0 | 1 1 |
| N²-(cyclohexylmethyl)-N¹-(2,6-dichlorophenyl)-4-methyl-1,2,3-thiadiazole-5-carboxamidine hydrochloride | 1 1 | 1 2 | 1 0 | 1 0 | 0 1 | 0 0 | 0 1 | 0 1 |
| N²-(cyclohexylmethyl)-N¹-(3,5-dichlorophenyl)-4-methyl-1,2,3-thiadiazole-5-carboxamidine hydrochloride | 0 2 | 0 2 | 0 0 | 0 0 | 0 0 | 0 0 | 0 0 | 0 0 |
| N¹-(4-chloro-2-methylphenyl)-N²-(cyclohexylmethyl)-4-methyl-1,2,3-thiadiazole-5-carboxamidine hydrochloride | 0 2 | 0 2 | 0 1 | 0 1 | 0 0 | 0 0 | 0 0 | 0 1 |
| N²-(cyclohexylmethyl)-N¹-(4-fluorophenyl)-4-methyl-1,2,3-thiadiazole-5-carboxamidine hydrochloride | 0 2 | 0 0 | 0 1 | 0 1 | 0 0 | 0 0 | 0 0 | 0 0 |
| N²-(cyclohexylmethyl)-N¹-(2-nitrophenyl)-4-methyl-1,2,3-thiadiazole-5-carboxamidine hydrochloride | 0 1 | 1 1 | 0 0 | 0 0 | 0 0 | 0 0 | 0 0 | 0 0 |
| N¹-(2-chloro-6-methylphenyl)-N²-(cyclohexylmethyl)-4-methyl-1,2,3-thiadiazole-5-carboxamidine hydrochloride | 1 2 | 0 1 | 1 2 | 0 1 | 0 1 | 0 0 | 0 1 | 0 1 |
| N²-(cyclohexylmethyl)-N¹-(phenyl)-4-methyl-1,2,3-thiadiazole-5-carboxamidine | 0 2 | 0 1 | 0 0 | 0 0 | 0 0 | 0 0 | 0 0 | 0 0 |
| N²-(4-chloro-2-methylphenyl)-N¹,N¹-(diethyl)-4-methyl-1,2,3-thiadiazole-5-carboxamidine | 0 0 | 0 2 | 0 0 | 0 1 | 0 0 | 0 0 | 0 0 | 0 0 |
| N²-(cyclohexylmethyl)-N¹,N¹-(diallyl)-4-methyl-1,2,3-thiadiazole-5-carboxamidine hydrochloride | 1 2 | 0 0 | 0 2 | 0 1 | 0 0 | 0 0 | 0 0 | 0 1 |
| N²-(3,4-dichlorophenyl)-N¹-(phenyl)-4-methyl-1,2,3-thiadiazole-5-carboxamidine | 0 2 | 0 0 | 0 0 | 0 0 | 0 0 | 0 0 | 0 0 | 0 0 |
| N¹-(4-chloro-2-methylphenyl)-N²-(phenyl)-4-methyl-1,2,3-thiadiazole-5-carboxamidine | 0 2 | 0 0 | 0 0 | 0 0 | 0 0 | 0 0 | 0 0 | 1 0 |
| N¹-(2-chlorophenyl)-N²-(4-chloro-2-methylphenyl)-4-methyl-1,2,3-thiadiazole-5-carboxamidine hydrochloride | 0 1 | 0 0 | 0 0 | 0 1 | 0 0 | 0 0 | 0 0 | 1 0 |
| N²-(cyclohexylmethyl)-N¹-(propyl)-4-methyl-1,2,3-thiadiazole-5-carboxamidine | 4 4 | 4 4 | 3 4 | 3 4 | 3 2 | 2 2 | 3 2 | 4 4 |
| N¹-(butyl)-N²-(cyclohexylmethyl)-4-methyl-1,2,3-thiadiazole-5-carboxamidine | 3 4 | 4 4 | 3 4 | 3 4 | 3 0 | 2 1 | 3 1 | 4 4 |
| N¹-(tert.-butyl)-N²-(cyclohexylmethyl)-4-methyl-1,2,3-thiadiazole-5-carboxamidine | 2 4 | 0 1 | 0 3 | 0 3 | 0 0 | 0 0 | 0 0 | 0 3 |
| N¹-(cyclohexyl)-N¹-(methyl)-N²-(cyclohexylmethyl)-4-methyl-1,2,3-thiadiazolecarboxamidine | 2 4 | 1 2 | 0 4 | 0 3 | 0 0 | 0 0 | 1 0 | 1 3 |
| N¹-(ethyl)-N¹-(cyclohexyl)-N²-(cyclohexylmethyl)-4-methyl-1,2,3-thiadiazole-5-carboxamidine | 1 2 | 0 1 | 0 0 | 0 0 | 1 0 | 0 0 | 0 0 | 0 3 |
| N¹-(allyl)-N¹-(cyclohexyl)-N²-(cyclohexylmethyl)-4-methyl-1,2,3-thiadiazole-5-carboxamidine | 1 4 | 0 1 | 0 1 | 0 1 | 0 0 | 0 0 | 0 0 | 0 2 |
| N²-(cyclohexylmethyl)-N¹,N¹-(diphenyl)-4-methyl-1,2,3-thiadiazole-5-carboxamidine | 3 4 | 3 3 | 1 4 | 3 4 | 1 0 | 2 0 | 1 1 | 1 4 |
| N²-(cyclohexylmethyl)-N¹-(1-methylpropyl)-4-methyl-1,2,3-thiadiazole-5-carboxamidine | 4 4 | 4 4 | 4 4 | 4 4 | 4 4 | 4 4 | 4 4 | 4 4 |
| N²-(cyclohexylmethyl)-N¹-(2,3-dimethylphenyl)-4-methyl-1,2,3-thiadiazole-5-carboxamidine | 0 1 | 1 0 | 1 0 | 0 0 | 0 0 | 0 0 | 0 0 | 0 0 |
| N²-(cyclohexylmethyl)-N¹-(isopropyl)-4-methyl-1,2,3-thiadiazole-5-carboxamidine | 4 4 | 3 4 | 3 4 | 3 4 | 3 2 | 3 1 | 3 1 | 4 4 |
| N¹-ethyl-N¹-butyl-N²-(cyclohexylmethyl)-4-methyl-1,2,3-thiadiazole-5-carboxamidine | 4 4 | 3 3 | 3 2 | 3 3 | 3 1 | 2 1 | 2 1 | 2 3 |
| N¹-butyl-N¹-methyl-N²-(cyclohexylmethyl)-4-methyl-1,2,3-thiadiazole-5-carboxamidine | 3 4 | 3 3 | 1 4 | 1 4 | 3 0 | 2 1 | 2 1 | 0 4 |

-continued

| Compound Name | Si VN | So VN | Be VN | Go VN | Ho VN | Ze VN | Lo VN | Se VN |
|---|---|---|---|---|---|---|---|---|
| $N^2$-(cyclohexylmethyl)-$N^1,N^1$-(dibutyl)-4-methyl-1,2,3-thiadiazole-5-carboxamidine | 3 4 | 3 3 | 0 2 | 2 4 | 3 0 | 2 0 | 3 0 | 1 2 |
| $N^1$-ethyl-$N^1$-isopropyl-$N^2$-(cyclohexylmethyl)-4-methyl-1,2,3-thiadiazole-5-carboxamidine | 0 2 | 0 0 | 0 0 | 0 0 | 0 0 | 0 0 | 0 0 | 0 0 |
| $N^2$-(cyclohexylmethyl)-$N^1,N^1$-(dipropyl)-4-methyl-1,2,3-thiadiazole-5-carboxamidine | 3 4 | 3 3 | 2 2 | 3 4 | 3 0 | 3 0 | 3 0 | 2 2 |
| $N^2$-(cyclohexylmethyl)-$N^1,N^1$-(diisobutyl)-4-1,2,3-thiadiazole-5-carboxamidine | 2 4 | 2 1 | 0 1 | 1 2 | 0 0 | 0 0 | 0 0 | 0 0 |
| $N^2$-(cyclohexylmethyl)-N-(1,3-dimethylbutyl)-4-methyl-1,2,3-thiadiazole-5-carboxamidine | 1 4 | 2 1 | 0 1 | 0 2 | 1 0 | 0 0 | 0 0 | 0 2 |
| $N^2$-(cyclohexylmethyl)-$N^1$-(1,1,3,3-tetramethylbutyl)-4-methyl-1,2,3-thiadiazole-5-carboxamidine | 2 4 | 2 1 | 0 3 | 1 3 | 1 0 | 1 1 | 1 0 | 1 1 |
| $N^2$-(cyclohexylmethyl)-$N^1$-3,5-dimethylphenyl)-4-methyl-1,2,3-thiadiazole-5-carboxamidine | 0 0 | 0 0 | 0 0 | 0 1 | 0 1 | 0 0 | 0 0 | 0 0 |
| $N^2$-(cyclohexylmethyl)-$N^1$-(2,4-dimethylphenyl)-4-methyl-1,2,3-thiadiazole-5-carboxamidine | 0 1 | 0 1 | 0 1 | 0 1 | 0 0 | 0 0 | 0 0 | 0 0 |
| $N^2$-(cyclohexylmethyl)-$N^1$-(2,5-dimethylphenyl)-4-methyl-1,2,3-thiadiazole-5-carboxamidine | 0 1 | 0 1 | 0 1 | 0 1 | 0 0 | 0 0 | 0 0 | 0 0 |
| $N^2$-(cyclohexylmethyl)-$N^1$-(2,6-dimethylphenyl)-4-methyl-1,2,3-thiadiazole-5-carboxamidine | 0 1 | 0 1 | 0 1 | 0 1 | 0 0 | 0 0 | 0 0 | 0 0 |
| $N^2$-(cyclohexylmethyl)-$N^1$-(3,4-dimethylphenyl)-4-methyl-1,2,3-thiadiazole-5-carboxamidine | 0 1 | 0 1 | 0 1 | 0 1 | 0 0 | 0 0 | 0 0 | 0 0 |
| $N^1$-(benzyl)-$N^2$-(cyclohexylmethyl)-4-methyl-1,2,3-thiadiazole-5-carboxamidine | 3 4 | 3 4 | 2 4 | 2 3 | 0 2 | 0 0 | 2 4 | 2 3 |
| $N^1,N^2$-bis(cyclohexylmethyl)-4-methyl-1,2,3-thiadiazole-5-carboxamidine | 2 4 | 1 1 | 0 3 | 0 0 | 1 1 | 1 1 | 0 0 | 0 0 |
| $N^1$-(cyclohexyl)-$N^2$-(cyclohexylmethyl)-4-methyl-1,2,3-thiadiazole-5-carboxamidine | 4 4 | 4 4 | 4 4 | 4 4 | 3 3 | 3 2 | 2 4 | 3 4 |
| $N^2$-(cyclohexylmethyl)-$N^1,N^1$-(tetramethylene)-4-methyl-1,2,3-thiadiazole-5-carboxamidine | 4 4 | 4 4 | 4 4 | 4 4 | 4 4 | 4 3 | 4 3 | 4 4 |
| $N^2$-(cyclohexylmethyl)-$N^1,N^1$-(pentamethylene)-4-methyl-1,2,3-thiadiazole-5-carboxamidine | 4 4 | 4 4 | 4 4 | 4 4 | 4 3 | 4 3 | 4 4 | 4 4 |
| $N^2$-(cyclohexylmethyl)-$N^1,N^1$-diisopropyl)-4-methyl-1,2,3-thiadiazole-5-carboxamidine | 0 4 | 0 4 | 0 4 | 0 4 | 0 0 | 0 2 | 0 0 | 0 4 |
| $N^2$-(cyclohexylmethyl)-$N^1,N^1$-(dihexyl)-4-methyl-1,2,3-thiadiazole-5-carboxamidine | 0 4 | 0 4 | 0 4 | 0 4 | 2 3 | 1 2 | 0 0 | 0 4 |
| $N^2$-(cyclohexylmethyl)-$N^1$-(1,2,2-trimethylpropyl)-4-methyl-1,2,3-thiadiazole-5-carboxamidine | 0 4 | 0 3 | 0 4 | 0 4 | 1 1 | 2 3 | 0 0 | 0 4 |
| $N^2$-(cyclohexylmethyl)-$N^1$-(3-methylbutyl)-4-methyl-1,2,3-thiadiazole-5-carboxamidine | 4 4 | 4 4 | 4 4 | 4 4 | 4 4 | 3 2 | 4 2 | 4 4 |
| $N^1$-(ethyl)-$N^1$-(propyl)-$N^2$-cyclohexylmethyl)-4-methyl-1,2,3-thiadiazole-5-carboxamidine | 4 4 | 4 4 | 4 4 | 4 4 | 4 2 | 3 2 | 4 2 | 4 3 |
| $N^2$-(cyclohexylmethyl)-$N^1$-(1,1-dimethylpropyl)-4-methyl-1,2,3-thiadiazole-5-carboxamidine | 4 4 | 4 2 | 2 3 | 0 2 | 1 0 | 0 0 | 3 0 | 2 0 |
| 4-methyl-5-[(cyclohexylmethylimino)-imidazole-1-yl)-methyl]-1,2,3-thiadiazole | 4 4 | 4 4 | 4 4 | 4 4 | 4 4 | 4 4 | 4 4 | 4 4 |
| 4-methyl-5-[(cyclohexylmethylimino)-(1,2,4-triazole-1-yl)-methyl]-1,2,3-thiadiazole | 4 4 | 4 4 | 4 4 | 4 4 | 4 3 | 4 3 | 4 4 | 4 4 |
| $N^2$-(cyclohexylmethyl)-$N^1$-(1,2-dimethylpropyl)-4-methyl-1,2,3-thiadiazole-5-carboxamidine | 0 2 | 0 2 | 0 2 | 0 0 | 0 0 | 0 0 | 0 0 | 0 0 |
| $N^1$-(allyl)-$N^2$-(cyclohexylmethyl)-4-methyl-1,2,3-thiadiazole-5-carboxamidine | 4 4 | 4 4 | 4 4 | 4 4 | 4 2 | 4 2 | 4 4 | 4 4 |
| $N^1$-(ethyl)-$N^2$-(cyclohexylmethyl)- | | | | | | | | |

| Compound Name | Si V N | So V N | Be V N | Go V N | Ho V N | Ze V N | Lo V N | Se V N |
|---|---|---|---|---|---|---|---|---|
| 4-methyl-1,2,3-thiadiazole-5-carboxamidine | 4 4 | 4 4 | 4 4 | 4 4 | 4 2 | 4 2 | 4 4 | 4 4 |
| $N^2$-(cyclohexylmethyl)-$N^1$-(methyl)-4-methyl-1,2,3-thiadiazole-5-carboxamidine | 4 4 | 4 4 | 4 4 | 4 4 | 4 2 | 4 2 | 4 4 | 4 4 |
| 4-methyl-1,2,3-thiadiazole-5-thiocarboxylic acid-(1,2,3,4-tetrahydro-1-naphthyl)-amide | 0 1 | 0 0 | 0 0 | 0 1 | 0 0 | 0 0 | 0 0 | 0 0 |
| 4-methyl-1,2,3-thiadiazole-5-thiocarboxylic acid-(cycloheptylmethyl)-amide | 1 2 | 1 2 | 1 2 | 1 3 | 1 1 | 1 1 | 2 2 | 1 2 |
| 4-methyl-1,2,3-thiadiazole-5-thiocarboxylic acid-(2-fluorobenzyl)-amide | 0 1 | 0 2 | 0 1 | 0 0 | 0 0 | 0 0 | 0 1 | 0 1 |
| 4-methyl-1,2,3-thiadiazole-5-thiocarboxylic acid-(cyclooctylmethyl)-amide | 2 2 | 1 2 | 1 2 | 0 1 | 0 1 | 0 1 | 0 2 | 0 2 |
| 4-methyl-1,2,3-thiadiazole-5-[N-cyclohexylmethyl-thiocarboximide acid-(4-chlorophenyl)-ester] | 4 4 | 4 4 | 4 4 | 4 4 | 4 4 | 3 2 | 4 4 | 4 4 |
| $N^2$-(cyclohexylmethyl)-$N^1,N^1$-(dimethyl)-4-methyl-1,2,3-thiadiazole-5-carboxamidine | 4 4 | 4 4 | 4 4 | 4 4 | 4 2 | 3 2 | 4 4 | 4 4 |
| $N^2$-(cyclohexylmethyl)-4-methyl-1,2,3-thiadiazole-5-carboxamidine hydrochloride | 4 4 | 4 4 | 3 4 | 3 3 | 2 2 | 2 2 | 3 4 | 3 3 |
| $N^2$-(4-chloro-2-methylphenyl)-$N^1,N^1$-(dimethyl)-4-methyl-1,2,3-thiadiazole-5-carboxamidine | 2 2 | 1 2 | 0 2 | 1 2 | 1 0 | 0 0 | 1 0 | 1 0 |
| $N^2$-(4-chloro-2-methylphenyl)-$N^1$-(methyl)-4-methyl-1,2,3-thiadiazole-5-carboxamidine | 1 2 | 1 2 | 0 1 | 1 1 | 1 0 | 0 0 | 1 0 | 1 0 |
| $N^1$-(methyl)-$N^2$-(methyl)-4-methyl-1,2,3-thiadiazole-5-carboxamidine | 1 0 | 1 0 | 0 0 | 0 0 | 0 0 | 0 0 | 0 0 | 0 0 |
| $N^1,N^1$-(dimethyl)-$N^2$-(methyl)-1,2,3-thiadiazole-5-carboxamidine | 1 0 | 1 0 | 0 0 | 0 0 | 0 0 | 0 0 | 0 0 | 0 0 |
| 4-methyl-1,2,3-thiadiazole-5-thiocarbonsaeure-benzylamide | 0 4 | 0 2 | 0 3 | 0 0 | 0 0 | 0 1 | 0 0 | 0 4 |
| 4-methyl-1,2,3-thiadiazole-5-thiocarboxylic acid-(3-methyl-cyclohexyl)-amide | 4 4 | 4 4 | 4 4 | 2 2 | 3 0 | 2 0 | 4 2 | 3 3 |
| 4-methyl-1,2,3-thiadiazole-5-thiocarboxylic acid-(2-methyl-cyclohexyl)-amide | 3 4 | 3 4 | 3 4 | 0 0 | 2 0 | 0 0 | 3 0 | 2 0 |
| 4-methyl-1,2,3-thiadiazole-5-thiocarboxylic acid-(4-fluorobenzyl)-amide | 4 4 | 4 4 | 4 3 | 0 2 | 2 0 | 0 0 | 3 0 | 3 4 |
| 4-methyl-1,2,3-thiadiazole-5-thiocarboxylic acid-(N-methyl-N-cyclohexylmethyl)-amide | 0 2 | 0 1 | 0 1 | 0 0 | 0 0 | 0 0 | 0 0 | 0 0 |
| Untreated | 0 0 | 0 0 | 0 0 | 0 0 | 0 0 | 0 0 | 0 0 | 0 0 |

EXAMPLE 8

The plants shown in the following table were treated with the compounds of the present invention, before germination at a rate of 1 kg per hectare. The compound was poured evenly on the soil, after seeding as a suspension at a rate of 500 liter water per hectare. The results show that the compounds destroy the known weeds and the soya beans remain unharmed.

| Compound | Soya | Ipomoea | Avenea | Alopecurus | Echinochloa | Setaria | Digitaria | Cyperus | Sorghum | Poa | Solanum | Datura | Escholtzia | Kochia |
|---|---|---|---|---|---|---|---|---|---|---|---|---|---|---|
| $N^2$-(cyclohexylmethyl-$N^1$-(1-methylpropyl)-4-methyl-1,2,3-thiadiazole-5-carboxamidine | 10 | 0 | 0 | 0 | 0 | 0 | 0 | 0 | 0 | 0 | 0 | 0 | 0 | 0 |
| Untreated | 10 | 10 | 10 | 10 | 10 | 10 | 10 | 10 | 10 | 10 | 10 | 10 | 10 | 10 |

0 = total destruction
10 = unharmed

EXAMPLE 9

Cotton plants in stage when it has 6 to 7 fully unfolded leaves were sprayed with the following compounds in the form of an aqueous emulsion or suspension in an application quantity of 500 liter water per hectare (repeated 4 times). Nine days after the application fallen leaves were counted and percentage calculated.

| | kg/ha | % defoliation |
|---|---|---|
| Compound | | |
| 4-methyl-1,2,3-thiadiazole-5-thiocarboxylic acid-(cyclohexylmethyl)-amide | 0.05 | 88.5 |
| Compound for Comparison | | |
| tri-n-butyl-trithiophosphate | 0.5 | 65.4 |

EXAMPLE 10

Cotton plants in stage when it has 5 to 6 unfolded leaves were sprayed with the following compounds in a dosage quantity of 0.5 kg in 500 liters of water per hectare (repeated four times). Fourteen days after the application the fallen leaves were counted and are tabulated as a percentage of the total number treated.

| Compound Name | kg/ha | % leaf fall |
|---|---|---|
| 4-methyl-1,2,3-thiadiazole-5-(N-cyclohexyl-methyl-carboximide chloride) | 0.5 | 86.4 |
| $N^2$-(cyclohexylmethyl)-$N^1$,$N^1$-(diethyl)-4-methyl-1,2,3-thiadiazole-5-carboxamidine | 0.5 | 86.4 |
| 4-methyl-1,2,3-thiadiazole-5-(N-cyclohexylmethyl-thiocarboximide acid-methyl-ester) | 0.5 | 82.6 |
| 4-methyl-1,2,3-thiadiazole-5-(N-cyclohexylmethyl-thiocarboximide acid benzylester) | 0.5 | 95.7 |
| 4-methyl-1,2,3-thiadiazole-5-(N-cyclohexylmethyl-thiocarboximide acid-(4-chlorobenzyl)-ester) | 0.5 | 87.0 |
| 4-methyl-1,2,3-thiadiazole-5-(N-cyclohexylmethyl-thiocarboximide acid-phenylester) | 0.5 | 77.8 |
| 4-methyl-1,2,3-thiadiazole-5-(N-cyclohexylmethyl-thiocarboximide acid-(4-methylphenyl)-ester | 0.5 | 81.5 |

EXAMPLE 11

Cotton plants in stage when it has 5 to 6 unfolded leaves were sprayed with the following compounds in a dosage quantity of 0.5 kg, in 500 liters of water per hectare (repeated four times). Six days after the application the fallen leaves were counted and are tabulated as a percentage of the total number treated.

| Compound | kg/ha | % leaf fall |
|---|---|---|
| $N^1$-(butyl)-$N^2$-(cyclohexylmethyl)-4-methyl-1,2,3-thiadiazole-5-carboxamidine | 0.05 | 50.0 |

EXAMPLE 12

In a hothouse, cucumbers before germination were treated with the compounds of the present invention at a rate of 0.3 kg/1.0 kg or 3 kg per hectare respectively. The compounds are prepared as 20% aqueous emulsions and sprayed in a quantity of 500 liters per hectare.

Three weeks after the treatment the growth effect of the first leaf was noted by measuring its length and breadth. The measurements were compared with the control plants which were not treated. The results indicate that the ones which were treated with the compounds had highly enlarged leaves. Also the treated plants were deep green in color.

| Compound | kg/ha | in % | in % |
|---|---|---|---|
| 4-methyl-1,2,3-thiadiazole-5-(N-cyclohexylmethyl-carboximide chloride) | 0.3 | 102 | 106 |
| | 1.0 | 118 | 110 |
| | 3.0 | 134 | 143 |
| Untreated | — | 100 | 100 |

EXAMPLE 13

Prophylactic treatment of leaves of grapevine against *plasmopara viticola* in hothouse.

Early grapevine leaves with about 5 to 8 leaves were sprayed with a mist of the concentrated compound. After the coated layer was dry, the underside of the leaves was sprayed with an aqueous solution of spores of fungus (about 20000 per ml) and then the leaves were incubated in a hothouse at 22° to 24° C., preferably in a water vapor saturated atmosphere. After the second day the humidity was reduced to normal level (30 to 70% saturation) for three to four days and then for one day it was raised to water vapor saturation. Finally on each leaf the percent of fungus infected area was measured and the fungicide effectiveness calculated as follows:

$$100 - \frac{100 \times \text{infection in treated leaves}}{\text{infection in untreated leaves}} = \% \text{ effectiveness}$$

The Compounds were formulated as 20% spray dust.

| | % effectiveness afetr treating dose % | |
|---|---|---|
| Compounds | 0,025 | 0,005 |
| 4-Methyl-1,2,3-thiadiazole-5-(N-cyclohexylmethyl-carboximidchloride) | | 95 |
| 4-Methyl-1,2,3-thiadiazole-5-/N-phenylcarboximide chloride] | 90 | |
| 4-Methyl-1,2,3-thiadiazole-5-thiocarboxylic acid-(cyclohexylmethyl)-amide | | 93 |
| 4-Methyl-1,2,3-thiadiazole-5-/N-cyclohexylmethyl-thiocarboximide acid methylester] | | 99 |
| 4-Methyl-1,2,3-thiadiazole-5-/N-cyclohexylmethyl-thiocarboximide acid benzylester] | 100 | 50 |
| 4-Methyl-1,2,3-thiadiazole-5-/N-cyclohexylmethyl-thiocarboximide acid-(4-chlorobenzyl)-ester] | 90 | 60 |
| 4-Methyl-1,2,3-thiadiazole-5-/N-cyclohexylmethyl-thiocarboximide acid ethylester] | | 100 |
| 4-Methyl-1,2,3-thiadiazole-5-(N-cyclohexylmethyl-thiocarboximide acid phenylester) | | 100 |
| 4-Methyl-1,2,3-thiadiazol-5- | | |

| Compounds | % effectiveness after treating dosage level | |
|---|---|---|
| | 0,025 | 0,025 |
| /N-cyclohexylmethyl-thiocarb-oximide acid-(4-methylphenyl)-ester] | 100 | |
| N²-(Cyclohexylmethyl)-N¹,N¹-(diethyl)-4-methyl-1,2,3-thiadiazole 5-carboxamidine | 100 | 75 |
| N²-(Cyclohexylmethyl)-N¹-(phenyl)-4-methyl-1,2,3-thiadiazole-5-carboxamidine, Hydrochloride | 90 | |
| N²-(Cyclohexylmethyl)-N¹-(phenyl)-N¹-(methyl)-4-methyl-1,2,3-thiadiazole-5-carboxamidine Hydrochloride | 99 | 79 |

| Compounds | % effectiveness after a dosage level % of | |
|---|---|---|
| | 0,025 | 0,025 |
| N²-(3,4-Dichlorophenyl)-N¹-(phenyl)-4-methyl-1,2,3-thiadiazole-5-carboxamidine | 85 | 82 |
| N¹-(2-Chlorophenyl)-N²-(4-chloro-2-methylphenyl)-4-methyl-1,2,3-thiadiazole-5-carboxamidine, Hydrochloride | 90 | |
| N²-(Cyclohexylmethyl)-N¹-(propyl)-4-methyl-1,2,3-thiadiazole-5-carboxamidine | | 98 |
| N¹-(Butyl)-N-(Cyclohexylmethyl)-4-methyl-1,2,3-thiadiazole-5-carboxamidine | | 96 |

EXAMPLE 14

Prophylactic treatment of leaves of pumpkin plants against *Erysiphe cichoroacearum* in hothouse Early pumpkin plant leaves were sprayed with a mist of the required concentration of the compound. After the leaves were dry, they were inoculated with dried mildew spores dust of *Erysiphe cichoracearum* and incubated at 24° C. After a week, the mildew infected area was measured as a percent of the total leaf surface area and the fungicide effectiveness is determined as follows:

$$100 - \frac{100 \times \text{infection in treated leaves}}{\text{infection in untreated}} = \% \text{ effectiveness}$$

The compounds were formulated as 20% spraydust.

| Compound | % effectiveness after treating dosage level | |
|---|---|---|
| | 0,025 | 0,005 |
| 4-Methyl-1,2,3-thiadiazole-5-(N-cyclohexylmethyl-carboximide chloride) | 96 | 45 |
| 4-Methyl-1,2,3-thiadiazole-5-thiocarboxylic acid-(cyclohexylmethyl)-amide | 100 | 93 |
| 4-Methyl-1,2,3-thiadiazole-5-/N-cyclohexylmethyl-thiocarb-oximide acid methylester] | 87 | 60 |
| 4-Methyl-1,2,3-thiadiazole-5-/N-cyclohexylmethyl-thiocarb-oximide acid benzylester] | 91 | 65 |
| 4-Methyl-1,2,3-thiadiazole-5-/N-cyclohexylmethyl-thiocarb-oximide acid-(4-chlorobenzyl)-ester] | 96 | 65 |
| 4-Methyl-1,2,3-thiadiazole-5-/N-cyclohexylmethyl-thiocarb-oximide acid ethylester] | 92 | 35 |
| 4-Methyl-1,2,3-thiadiazole-5-(N-cyclohexylmethyl-thiocarb-oximide acid phenylester) | 94 | 60 |
| 4-Methyl-1,2,3-thiadiazole-5-/N-cyclohexylmethyl-thiocarb-oximide acid-(4-methylphenyl)-ester] | 96 | 55 |
| N²-(Cyclohexylmethyl)-N¹,N¹-(diethyl)-4-methyl-1,2,3-thiadiazole-5-carboxamidine | 92 | 90 |
| N²-(Cyclohexylmethyl)-N¹-2-methylphenyl)-4-methyl-1,2,3-thiadiazole-5-carboxamidine Hydrochloride | 97 | 91 |
| N²-(Cyclohexylmethyl)-N¹-(3-methylphenyl-1,2,3-thiadiazole-5-carboxamidine Hydrochloride | 100 | 92 |
| N²-(Cyclohexylmethyl)-N¹-(4-methylphenyl)-4-methyl-1,2,3-thiadiazole-5-carboxamidine Hydrochloride | 99 | 92 |

| Compound | % effectiveness after a dosage level % of | |
|---|---|---|
| | 0,025 | 0,005 |
| N²-(Cyclohexylmethyl)-N¹-(propyl)-4-methyl-1,2,3-thiadiazole-5-carboxamidine | | 100 |
| N¹-(Butyl)-N²-(cyclohexylmethyl)-4-methyl-1,2,3-thiadiazole-5-carboxamidine | 97 | 92 |
| N¹-(tert.-Butyl)-N²-(cyclohexylmethyl)-4-methyl-1,2,3-thiadiazole-5-carboxamidine | 99 | 85 |
| N²-(Cyclohexylmethyl)-N¹,N¹-(diphenyl)-4-methyl-1,2,3-thiadiazole-5-carboxamidine | 98 | 93 |

EXAMPLE 15 prophylactic treatment of rice seedling leaves against Piricularia Oryzae in a hothouse Early rice plants are sprayed with a mist of the concentra of Compounds as shown in the following tables. After the plants were dry, they, as well as the untreated control plants were inoculated with leaf spot starter *piricularia orzyae* through a spray of a suspension of spores (about 200,000/ml), and incubated in humid atmosphere at 25° to 27° C. in a hothouse. After 5 days the percent of infected leaf area was determined. The fungicide effectiveness is calculated as follows:

$$100 - \frac{100 \times \text{infection in treated}}{\text{infection in untreated}} = \% \text{ effectiveness}$$

The Compounds were formulated as 20% Spraydust.

| Compound | % effectiveness after a dosage level of 0.1% |
|---|---|
| 4-Methyl-1,2,3-thiadiazol-5-/N-(2,6-dimethylphenyl)-carboximide chloride] | 100 |
| N²-(Cyclohexylmethyl)-N¹-(phenyl)-4-methyl-1,2,3-thiadiazole-5-carboxamidine, Hydrochloride | 80 |
| N²-(3,4-Dichlorophenyl)-N¹-(phenyl)-4-methyl-1,2,3-thiadiazole-5-carboxamidine | 73 |

EXAMPLE 16

Seed treatment against *Helminthosporium gramineum*

Barley seed naturally infected with *Helminthosporium gramineum* is treated as shown in the table and compared with the untreated one. Seed sowed in a claypot filled with soil and allowed to germinate at a temperature lower than 16° C. After swelling the buds are exposed to artificial light for a period of 12 hours daily. After about 5 weeks the germinated as well as the fungus infected plants of each test sample are counted. The fungicide effectiveness is figured out as follows:

$$100 - \frac{100 \times \text{infection in treated}}{\text{infection in untreated}} = \% \text{ effectiveness}$$

The compounds have 20% concentration.

| Compound | % effectiveness after treating the seed with 50g compound per 100 kg seed |
|---|---|
| 4-Methyl-1,2,3-thiadiazole-5-[N-(3-methylphenyl)-carboximide chloride] | 100 |
| 4-Methyl-1,2,3-thiadiazole-5-[N-(4-methylphenyl)-carboximide chloride] | 80 |
| 4-Methyl-1,2,3-thiadiazole-5-[N-(4-fluorophenyl)-carboximide chloride] | 80 |
| 4-Methyl-1,2,3-thiadiazole-5-[N-(2-chlorophenyl)-carboximide chloride] | 71 |
| 4-Methyl-1,2,3-thiadiazole-5-[N-phenylcarboximide chloride] | 71 |

EXAMPLE 17

Seed treatment against *tilletia caries* Wheat seed was contaminated with spores of stinking smut starter (bunt) *tilletia caries*. The rate was 3 g spores per kg of seed. The bearded ends of the untreated grains as well as the ones treated according to the table below were pressed into a petri dish filled with a substrate of moist loam, and incubated for 3 days at a temperature lower than 120° C. Subsequently the grains were taken out and the petri dish containing the remaining stinking smut spores was further incubated at 12° C. 10 days later the spores were tested for germination. The fungicide effectiveness is figured out as follows:

$$100 - \frac{100 \times \text{germ percent in treated}}{\text{germ percent in untreated}} = \% \text{ effectiveness}$$

The Compounds have 20% concentration

| Compound | % effectiveness of 20 g compound per 100 kg seed |
|---|---|
| 4-Methyl-1,2,3-thiadiazole-5-(N-cyclohexylmethylcarboximide chloride) | 100 |
| 4-Methyl-1,2,3-thiadiazole-5-/N-(3,4-dichlorophenyl)-carboximide chloride] | 90 |
| 4-Methyl-1,2,3-thiadiazole-5-/N-(4-fluorobenzyl)-carboximide-chloride] | 75 |
| 4-Methyl-1,2,3-thiadiazole-5-/N-(2,6-dimethylphenyl)-carboximide chloride] | 90 |
| 4-Methyl-1,2,3-thiadiazole-5-thiocarboxylic acid (cyclohexylmethyl)-amide | 75 |
| 4-Methyl-1,2,3-thiadiazole-5-/N-cyclohexylmethyl-thiocarboximide acid methylester] | 100 |
| 4-Methyl-1,2,3-thiadiazole-5-/N-cyclohexyl-methyl-thiocarboximide acid benzylester] | 100 |
| 4-Methyl-1,2,3-thiadiazole-5-/N-cyclohexylmethyl-thiocarboximide acid-(4-chlorobenzyl)-ester] | 90 |
| 4-Methyl-1,2,3-thiadiazole-5-/N-cyclohexylmethyl-thiocarboximide acid ethylester] | 90 |
| 4-Methyl-1,2,3-thiadiazole-5-(N-cyclohexylmethyl-thiocarboximide acid phenylester) | 90 |
| 4-Methyl-1,2,3-thiadiazole-5-/N-cyclohexylmethyl-thiocarboximide acid-(4-methylphenyl)-ester] | 100 |
| $N^2$-(Cyclohexylmethyl)-$N^1$,$N^1$-(diethyl)-4-methyl-1,2,3-thiadiazole-5-carboxamidine | 100 |
| $N^2$-(Cyclohexylmethyl)-$N^1$,$N^1$-(diallyl)-4-methyl-1,2,3-thiadiazole-5-carboxamidine Hydrochloride | 90 |
| $N^2$-(Cyclohexylmethyl)-$N^1$-(propyl)-4-methyl-1,2,3-thiadiazole-5-carboxamidine | 90 |
| $N^1$-(Butyl)-$N^2$-(cyclohexylmethyl)-4-methyl-1,2,3-thiadiazole-5-carboxamidine | 100 |
| $N^2$-(Cyclohexylmethyl)-$N^1$-(1-methylpropyl)-4-methyl-1,2,3-thiadiazole-5-carboxamidine | 90 |

It will be understood that the above description of the present invention is susceptible to various modifications changes and adaptations and the same are intended to be comprehended within the meaning and range of equivalents of the appended claims.

We claim:

1. 1,2,3-Thiadiazole-5-carboxylic acid compounds of the general formula

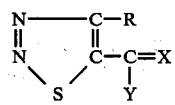

wherein
R is hydrogen or methyl,
y is chloro, amino, methylamino, ethylamino, propylamino, methylpropylamino, isopropylamino, 1,1-dimethylpropylamino, 1,2,2-trimethylpropylamino, butylamino, tert.butylamino, 3-methylbutylamino, 1,3-dimethylbutylamino, 1,1,3,3-tetramethylbutylamino, N,N-dimethylamino, N,N-diethylamino, N,N-diisopropylamino, N,N-dipropylamino, N,N-dibutylamino, N,N-diisobutylamino, N,N-dihexylamino, N-methyl-N-butylamino, N-ethyl-N-propylamino, N-ethyl-N-isopropylamino, N-ethyl-N-butylamino, allylamino, N,N-diallylamino, cyclohexylamino, N-methyl-N-cyclohexylamino, N-ethyl-N-cyclohexylamino, N-allyl-N-cyclohexylamino, phenylamino, methylphenylamino, dimethylphenylamino, halogenophenylamino, dichlorophenylamino, chloromethylphenylamino, nitrophenylamino, N-phenyl-N-methyl-amino, N,N-diphenylamino, cyclohexylmethylamino, benzylamino, N,N-tetramethylenamino, N,N-pentamethylenamino, imidazolyl-1,1,2,4-triazolyl-1, methylmercapto, ethylmercapto, phenylmercapto, methylphenylmercapto, benzylmercapto or chlorobenzylmercapto and X is methylimino, phenylimino, methylphenylimino, dimethylphenylimino, halogenophenylimino, dihalogenophenylimino, chloromethylphenylimino, benzylimino, halogenobenzylimino, or cyclohexylmethylimino, or an acid addition salt thereof.

2. The compound as defined in claim 1 which is 4-methyl-1,2,3-thiadiazole-5-(N-cyclohexylmethyl)-carboximide chloride.

3. The compound as defined in claim 1 which is 4-methyl-1,2,3-thiadiazole-5-[N-(3,4-dichlorophenyl)-carboximide chloride].

4. The compound as defined in claim 1 which is 4-methyl-1,1,3-thiadiazole-5-[N-(4-chloro-2-methylphenyl)-carboximide chloride].

5. The compound as defined in claim 1 which is 4-methyl-1,2,3-thiadiazole-5-[N-(3-chlorophenyl)-carboximide chloride].

6. The compound as defined in claim 1 which is 4-methyl-1,2,3-thiadiazole-5-[N-(4-chlorophenyl)-carboximide chloride].

7. The compound as defined in claim 1 which is 4-methyl-1,2,3-thiadiazole-5-[N-(2-methylphenyl)-carboximide chloride].

8. The compound as defined in claim 1 which is 4-methyl-1,2,3-thiadiazole-5-[N-(3-methylphenyl)-carboximide chloride].

9. The compound as defined in claim 1 which is 4-methyl-1,2,3-thiadiazole-5-[N-(4-methylphenyl)-carboximide chloride].

10. The compound as defined in claim 1 which is 4-methyl-1,2,3-thiadiazole-5-[N-(4-fluorophenyl)-carboximide chloride].

11. The compound as defined in claim 1 which is 4-methyl-1,2,3-thiadiazole-5-[N-(2-chlorophenyl)-carboximide chloride].

12. The compound as defined in claim 1 which is 4-methyl-1,2,3-thiadiazole-5-[N-(4-chlorobenzyl)-carboximide chloride].

13. The compound as defined in claim 1 which is 4-methyl-1,2,3-thiadiazole-5-[N-(4-fluorobenzyl)-carboximide chloride].

14. The compound as defined in claim 1 which is 4-methyl-1,2,3-thiadiazole-5-[N-phenylcarboximide chloride].

15. The compound as defined in claim 1 which is 4-methyl-1,2,3-thiadiazole-5-[N-(2,6-dimethylphenyl)-carboximide chloride].

16. The compound which is 4-methyl-1,2,3-thiadiazole-5-[N-cyclohexylmethyl-thiocarboximide acid methylester].

17. The compound which is 4-methyl-1,2,3-thiadiazole-5-[N-cyclohexylmethyl-thiocarboximide acid benzylester].

18. The compound which is 4-methyl-1,2,3-thiadiazole-5-[N-cyclohexylmethyl-thiocarboximide acid-(4-chlorobenzyl)-ester].

19. The compound which is 4-methyl-1,2,3-thiadiazole-5-[N-cyclohexylmethyl-thiocarboxymide acid ethylester].

20. The compound which is 4-methyl-1,2,3-thiadiazole-5-(N-cyclohexylmethyl-thiocarboximide acid phenylester).

21. The compound which is 4-methyl-1,2,3-thiadiazole-5-[N-cyclohexylmethyl-thiocarboximide acid-(4-methylphenyl)-ester].

22. The compound as defined in claim 1 which is $N^2$-(cyclohexylmethyl)-$N^1$,$N^1$-(diethyl)-4-methyl-1,2,3-thiadiazole-5-carboxamidine.

23. The compound as defined in claim 1 which is $N^2$-(cyclohexylmethyl)-$N^1$-(phenyl)-4-methyl-1,2,3-thiadiazole-5-carboxamidine.

24. The compound as defined in claim 1 which is $N^2$-(cyclohexylmethyl)-$N^1$-(phenyl)-$N^1$-(methyl)-4-methyl-1,2,3-thiadiazole-5-carboxamidine.

25. The compound as defined in claim 1 which is $N^1$-(2-chlorophenyl)-$N^2$-(cyclohexylmethyl)-4-methyl-1,2,3-thiadiazole-5-carboxamidine.

26. The compound as defined in claim 1 which is $N^1$-(3-chlorophenyl)-$N^2$-(cyclohexylmethyl)-4-methyl-1,2,3-thiadiazole-5-carboxamidine.

27. The compound as defined in claim 1 which is $N^1$-(4-chlorophenyl)-$N^2$-(cyclohexylmethyl)-4-methyl-1,2,3-thiadiazole-5-carboxamidine.

28. The compound as defined in claim 1 which is $N^2$-(cyclohexylmethyl)-$N^1$-(3,4-dichlorophenyl)-4-methyl-1,2,3-thiadiazole-5-carboxamidine.

29. The compound as defined in claim 1 which is $N^2$-(cyclohexylmethyl)-$N^1$-(2-methylphenyl)-4-methyl-1,2,3-thiadiazole-5-carboxamidine.

30. The compound as defined in claim 1 which is $N^2$-(cyclohexylmethyl)-$N^1$-(3-methylphenyl)-1,2,3-thiadiazole-5-carboxamidine.

31. The compound as defined in claim 1 which is $N^2$-(cyclohexylmethyl)-$N^1$-(4-methylphenyl)-4-methyl-1,2,3-thiadiazole-5-carboxamidine.

32. The compound as defined in claim 1 which is $N^2$-(cyclohexylmethyl)-$N^1$-(2,6-dichlorophenyl)-4-methyl-1,2,3-thiadiazole-5-carboxamidine.

33. The compound as defined in claim 1 which is $N^2$-(cyclohexylmethyl)-$N^1$-(3,5-dichlorophenyl)-4-methyl-1,2,3-thiadiazole-5-carboxamidine.

34. The compound as defined in claim 1 which is $N^1$-(4-chloro-2-methylphenyl)-$N^2$-(cyclohexylmethyl)-4-methyl-1,2,3-thiadiazole-5-carboxamidine.

35. The compound as defined in claim 1 which is $N^2$-(cyclohexylmethyl)-$N^1$-(4-fluorophenyl)-4-methyl-1,2,3-thiadiazole-5-carboxamidine.

36. The compound as defined in claim 1 which is $N^2$-(cyclohexylmethyl)-$N^1$-(2-nitrophenyl)-4-methyl-1,2,3-thiadiazole-5-carboxamidine.

37. The compound as defined in claim 1 which is $N^1$-(2-chloro-6-methylphenyl)-$N^2$-(cyclohexylmethyl)-4-methyl-1,2,3-thiadiazole-5-carboxamidine.

38. The compound as defined in claim 1 which is $N^2$-(cyclohexylmethyl)-$N^1$-(2,3-dimethylphenyl)-4-methyl-1,2,3-thiadiazole-5-carboxamidine.

39. The compound as defined in claim 1 which is $N^2$-(4-chloro-2-methylphenyl)-$N^1$,$N^1$-(diethyl)-4-methyl-1,2,3-thiadiazole-5-carboxamidine.

40. The compound as defined in claim 1 which is $N^2$-(cyclohexylmethyl)-$N^1$,$N^1$-(diallyl)-4-methyl-1,2,3-thiadiazole-5-carboxamidine.

41. The compound as defined in claim 1 which is $N^2$-(3,4-dichlorophenyl)-$N^1$-(phenyl)-4-methyl-1,2,3-thiadiazole-5-carboxamidine.

42. The compound as defined in claim 1 which is $N^1$-(4-chloro-2-methylphenyl)-$N^2$-(phenyl)-4-methyl-1,2,3-thiadiazole-5-carboxamidine.

43. The compound as defined in claim 1 which is $N^1$-(2-chlorophenyl)-$N^2$-(4-chloro-2-methylphenyl)-4-methyl-1,2,3-thiadiazole-5-carboxamidine.

44. The compound as defined in claim 1 which is $N^2$-(cyclohexylmethyl)-$N^1$-(propyl)-4-methyl-1,2,3-thiadiazole-5-carboxamidine.

45. The compound as defined in claim 1 which is $N^1$-(butyl)-$N^2$-(cyclohexylmethyl)-4-methyl-1,2,3-thiadiazole-5-carboxamidine.

46. The compound as defined in claim 1 which is $N^1$-(tert.-butyl)-$N^2$-(cyclohexylmethyl)-4-methyl-1,2,3-thiadiazole-5-carboxamidine.

47. The compound as defined in claim 1 which is $N^1$-(cyclohexyl)-$N^1$-(methyl)-$N^2$-(cyclohexylmethyl)-4-methyl-1,2,3-thiadiazole-5-carboxamidine.

48. The compound as defined in claim 1 which is $N^1$-(ethyl)-$N^1$-(cyclohexyl)-$N^2$-(cyclohexylmethyl-1,2,3-thiadiazole-5-carboxamidine.

49. The compound as defined in claim 1 which is $N^1$-(allyl)-$N^1$-(cyclohexyl)-$N^2$-(cyclohexylmethyl)-4-methyl-1,2,3-thiadiazole-5-carboxamidine.

50. The compound as defined in claim 1 which is $N^2$-(cyclohexylmethyl)-$N^1,N^1$-(diphenyl)-4-methyl-1,2,3-thiadiazole-5-carboxamidine.

51. The compound as defined in claim 1 which is $N^2$-(cyclohexylmethyl)-$N^1$-(1-methyl-propyl)-4-methyl-1,2,3-thiadiazole-5-carboxamidine.

52. The compound as defined in claim 1 which is $N^2$-(cyclohexylmethyl)-$N^1$-(isopropyl)-4-methyl-1,2,3-thiadiazole-5-carboxamidine.

53. The compound as defined in claim 1 which is $N^1$-ethyl-$N^1$-butyl-$N^2$-(cyclohexylmethyl)-4-methyl-1,2,3-thiadiazole-5-carboxamidine.

54. The compound as defined in claim 1 which is $N^1$-butyl-$N^1$-methyl-$N^2$-(cyclohexyl-methyl)-4-methyl-1,2,3-thiadiazole-5-carboxamidine.

55. The compound as defined in claim 1 which is $N^2$-(cyclohexylmethyl)-$N^1,N^1$-(dibutyl)-4-methyl-1,2,3-thiadiazole-5-carboxamidine.

56. The compound as defined in claim 1 which is $N^1$-ethyl-$N^1$-isopropyl-$N^2$-(cyclohexylmethyl)-4-methyl-1,2,3-thiadiazole-5-carboxamidine.

57. The compound as defined in claim 1 which is $N^2$-(cyclohexylmethyl)-$N^1,N^1$-(dipropyl)-4-methyl-1,2,3-thiadiazole-5-carboxamidine.

58. The compound as defined in claim 1 which is $N^2$-(cyclohexylmethyl)-$N^1,N^1$-(diisobutyl)-4-methyl-1,2,3-thiadiazole-5-carboxamidine.

59. The compound as defined in claim 1 which is $N^2$-(cyclohexylmethyl)-N-(1,3-dimethylbutyl)-4-methyl-1,2,3-thiadiazole-5-carboxamidine.

60. The compound as defined in claim 1 which is $N^2$-(cyclohexylmethyl)-$N^1$-(1,1,3,3-tetramethylbutyl)-4-methyl-1,2,3-thiadiazole-5-carboxamidine.

61. The compound as defined in claim 1 which is $N^2$-(cyclohexylmethyl)-$N^1$-(3,5-dimethylphenyl)-4-methyl-1,2,3-thiadiazole-5-carboxamidine.

62. The compound as defined in claim 1 which is $N^2$-(cyclohexylmethyl)-$N^1$-(2,4-dimethylphenyl)-4-methyl-1,2,3-thiadiazole-5-carboxamidine.

63. The compound as defined in claim 1 which is $N^2$-(cyclohexylmethyl)-$N^1$-(2,5-dimethylphenyl)-4-methyl-1,2,3-thiadiazole-5-carboxamidine.

64. The compound as defined in claim 1 which is $N^2$-(cyclohexylmethyl)-$N^1$-(2,6-dimethylphenyl)-4-methyl-1,2,3-thiadiazole-5-carboxamidine.

65. The compound as defined in claim 1 which is N-(cyclohexylmethyl)-N-(3,4-dimethylphenyl)-4-methyl-1,2,3-thiadiazole-5-carboxamidine.

66. The compound as defined in claim 1 which is $N^1$-(benzyl)-$N^2$-(cyclohexylmethyl)-4-methyl-1,2,3-thiadiazole-5-carboxamidine.

67. The compound as defined in claim 1 which is $N^1,N^2$-bis(cyclohexylmethyl)-4-methyl-1,2,3-thiadiazole-5-carboxamidine.

68. The compound as defined in claim 1 which is $N^1$-(cyclohexyl)-$N^2$-(cyclohexylmethyl)-4-methyl-1,2,3-thiadiazole-5-carboxamidine.

69. The compound as defined in claim 1 which is $N^2$-(cyclohexylmethyl)-$N^1,N^1$-(tetramethylene)-4-methyl-1,2,3-thiadiazole-5-carboxamidine.

70. The compound as defined in claim 1 which is $N^2$-(cyclohexylmethyl)-$N^1,N^1$-(diisopropyl)-4-methyl-1,2,3-thiadiazole-5-carboxamidine.

71. The compound as defined in claim 1 which is $N^2$-(cyclohexylmethyl)-$N^1,N^1$-(dihexyl)-4-methyl-1,2,3-thiadiazole-5-carboxamidine.

72. The compound as defined in claim 1 which is $N^2$-(cyclohexylmethyl)-$N^1$-(1,2,2-trimethylpropyl)-4-methyl-1,2,3-thiadiazole-5-carboxamidine.

73. The compound as defined in claim 1 which is $N^2$-(cyclohexylmethyl)-$N^1$-(3-methylbutyl)-4-methyl-1,2,3-thiadiazole-5-carboxamidine.

74. The compound as defined in claim 1 which is $N^1$-(ethyl)-$N^1$-(propyl)-$N^2$-(cyclohexylmethyl)-4-methyl-1,2,3-thiadiazole-5-carboxamidine.

75. The compound as defined in claim 1 which is $N^2$-(cyclohexylmethyl)-$N^1$-(1,1-dimethylpropyl)-4-methyl-1,2,3-thiadiazole-5-carboxamidine.

76. The compound as defined in claim 1 which is 4-methyl-5-[(cyclohexylmethylimino)-imidazole-1-yl)-methyl]-1,2,3-thiadiazole.

77. The compound as defined in claim 1 which is 4-methyl-5-[(cyclohexylmethylimino)-(1,2,4-triazole-1-ylmethyl]-1,2,3-thiadiazole.

78. The compound as defined in claim 1 which is $N^2$-(cyclohexylmethyl)-$N^1$-(1,2-dimethylpropyl)-4-methyl-1,2,3-thiadiazole-5-carboxamidine.

79. The compound as defined in claim 1 which is $N^1$-(allyl)-$N^2$-(cyclohexylmethyl)-4-methyl-1,2,3-thiadiazole-5-carboxamidine.

80. The compound as defined in claim 1 which is $N^1$-(ethyl)-$N^2$-(cyclohexylmethyl)-4-methyl-1,2,3-thiadiazole-5-carboxamidine.

81. The compound as defined in claim 1 which is $N^2$-(cyclohexylmethyl)-$N^1$-(methyl)-4-methyl-1,2,3-thiadiazole-5-carboxamidine.

82. The compound which is 4-methyl-1,2,3-thiadiazole-5-[N-cyclohexylmethyl-thiocarboximide acid-(4-chlorophenyl)-ester].

83. The compound as defined in claim 1 which is $N^2$-(cyclohexylmethyl-$N^1,N^1$-(dimethyl)-4-methyl-1,2,3-thiadiazole-5-carboxamidine.

84. The compound as defined in claim 1 which is $N^2$-(cyclohexylmethyl)-4-methyl-1,2,3-thiadiazole-5-carboxamidine hydrochloride.

85. The compound as defined in claim 1 which is $N^2$-(4-chloro-2-methylphenyl)-$N^1,N^1$-(dimethyl)-4-methyl-1,2,3-thiadiazole-5-carboxamidine.

86. The compound as defined in claim 1 which is $N^2$-(4-chloro-2-methylphenyl)-$N^1$-(methyl)-4-methyl-1,2,3-thiadiazole-5-carboxamidine.

87. The compound as defined in claim 1 which is $N^1$-(methyl)-$N^2$-(methyl)-4-methyl-1,2,3-thiadiazole-5-carboxamidine.

88. The compound as defined in claim 1 which is $N^1,N^1$-(dimethyl)-$N^2$-(methyl)-1,2,3-thiadiazole-5-carboxamidine.

89. The compound as defined in claim 1 which is $N^2$-(cyclohexylmethyl)-$N^1,N^1$-(pentamethylene)-4-methyl-1,2,3-thiadiazole-5-carboxamidine.

90. A herbicide and plant growth (controlling) regulating agent comprising (at least a small quantity) an effective amount of a 1,2,3-thiadiazole-5-carboxylic acid derivative of claim 1 in admixture with an inert carrier.

91. A fungicide comprising (at least a small quantity) an effective amount of a 1,2,3-thiadiazole-5-carboxylic acid derivative of claim 1 in admixture with an inert carrier.

92. Compounds of claim 1 further comprising a surface active agent.

93. Method of plant growth regulation which comprises applying to a plant and its habitat a plant growth regulating amount of a compound of claim 1.

* * * * *